(12) United States Patent
Fitzpatrick et al.

(10) Patent No.: US 12,048,937 B2
(45) Date of Patent: Jul. 30, 2024

(54) COMPACT REVERSE FLOW CENTRIFUGE SYSTEM

(71) Applicant: SCINOGY PRODUCTS PTY LTD, Mount Martha (AU)

(72) Inventors: Ian Fitzpatrick, Mount Martha (AU); David James, Mount Martha (AU); Stephen Wilson, Mount Martha (AU)

(73) Assignee: Scinogy Products Pty Ltd, Mount Martha (AU)

( * ) Notice: Subject to any disclaimer, the term of this patent is extended or adjusted under 35 U.S.C. 154(b) by 727 days.

(21) Appl. No.: 16/607,343

(22) PCT Filed: May 11, 2018

(86) PCT No.: PCT/AU2018/050449
§ 371 (c)(1),
(2) Date: Oct. 22, 2019

(87) PCT Pub. No.: WO2018/204992
PCT Pub. Date: Nov. 15, 2018

(65) Prior Publication Data
US 2020/0297911 A1    Sep. 24, 2020

(30) Foreign Application Priority Data

May 12, 2017 (AU) ................................ 2017901771
Jan. 22, 2018 (AU) ................................ 2018900193

(51) Int. Cl.
*B04B 5/06*    (2006.01)
*A61M 1/02*    (2006.01)
(Continued)

(52) U.S. Cl.
CPC ............. *B04B 5/06* (2013.01); *A61M 1/0259* (2013.01); *A61M 1/0272* (2013.01);
(Continued)

(58) Field of Classification Search
CPC .............. A61M 1/3604; A61M 1/3693; A61M 39/22; A61M 60/104; A61M 60/109;
(Continued)

(56) References Cited

U.S. PATENT DOCUMENTS 3,718,278 A * 2/1973 Conklin .................. B04B 11/08
494/79
3,986,442 A * 10/1976 Khoja ................... B04B 5/0442
475/182

(Continued)

FOREIGN PATENT DOCUMENTS

DE    27 01 976 A1    7/1978
EP    1110566 A2 *    6/2001    .............. A61M 1/34
(Continued)

OTHER PUBLICATIONS

Extended European Search Report issued on Feb. 8, 2021 in application No. 18798992.3; 7 pgs.
(Continued)

Primary Examiner — John Kim
(74) Attorney, Agent, or Firm — Knobbe Martens Olson & Bear LLP

(57) ABSTRACT

Provided is a chamber configuration for a reverse flow centrifuge, and a reverse flow centrifuge system configured for low fluid volume and small radius rotation. The compact reverse flow centrifuge system has a reusable subsystem and a single use replaceable subsystem. The replaceable subsystem comprises a separation chamber, fluid delivery manifold and rotational mounting connecting the separation chamber to the fluid manifold. The single use replaceable subsystem provides a closed environment for execution of reverse flow centrifugation processes. The separation chamber has a substantially conical fluid enclosure portion connected to a neck portion, and a dip tube extends centrally through the
(Continued)

conical fluid enclosure to provide a fluid path to the tip of the conical fluid enclosure.

21 Claims, 18 Drawing Sheets

(51) Int. Cl.

| | | |
|---|---|---|
| *A61M 1/26* | (2006.01) | |
| *A61M 1/30* | (2006.01) | |
| *A61M 1/34* | (2006.01) | |
| *A61M 1/36* | (2006.01) | |
| *A61M 39/10* | (2006.01) | |
| *A61M 39/12* | (2006.01) | |
| *A61M 39/22* | (2006.01) | |
| *A61M 39/28* | (2006.01) | |
| *A61M 60/10* | (2021.01) | |
| *A61M 60/104* | (2021.01) | |
| *A61M 60/109* | (2021.01) | |
| *B04B 1/06* | (2006.01) | |
| *B04B 5/04* | (2006.01) | |
| *B04B 5/12* | (2006.01) | |
| *B04B 7/00* | (2006.01) | |
| *B04B 9/02* | (2006.01) | |
| *B04B 11/04* | (2006.01) | |
| *B04B 13/00* | (2006.01) | |
| *C12M 1/00* | (2006.01) | |
| *C12M 1/12* | (2006.01) | |
| *C12M 1/26* | (2006.01) | |
| *C12M 3/04* | (2006.01) | |
| *G01N 33/49* | (2006.01) | |
| *A61M 39/02* | (2006.01) | |

(52) U.S. Cl.
CPC .......... *A61M 1/0281* (2013.01); *A61M 1/029* (2013.01); *A61M 1/26* (2013.01); *A61M 1/262* (2014.02); *A61M 1/308* (2014.02); *A61M 1/3496* (2013.01); *A61M 1/3604* (2014.02); *A61M 1/3606* (2014.02); *A61M 1/3616* (2014.02); *A61M 1/3621* (2013.01); *A61M 1/3622* (2022.05); *A61M 1/3693* (2013.01); *A61M 1/3696* (2014.02); *A61M 39/10* (2013.01); *A61M 39/1011* (2013.01); *A61M 39/105* (2013.01); *A61M 39/12* (2013.01); *A61M 39/22* (2013.01); *A61M 39/28* (2013.01); *A61M 60/104* (2021.01); *A61M 60/109* (2021.01); *B04B 1/06* (2013.01); *B04B 5/04* (2013.01); *B04B 5/0442* (2013.01); *B04B 5/12* (2013.01); *B04B 7/00* (2013.01); *B04B 9/02* (2013.01); *B04B 11/04* (2013.01); *B04B 13/00* (2013.01); *B04B 13/003* (2013.01); *C12M 23/26* (2013.01); *C12M 23/28* (2013.01); *C12M 27/10* (2013.01); *C12M 29/00* (2013.01); *C12M 33/10* (2013.01); *C12M 37/04* (2013.01); *C12M 47/04* (2013.01); *G01N 33/491* (2013.01); *A61M 1/3603* (2014.02); *A61M 2039/0276* (2013.01); *A61M 2039/226* (2013.01); *B04B 2005/0435* (2013.01); *B04B 2005/0464* (2013.01); *B04B 2005/0471* (2013.01); *B04B 2005/0478* (2013.01); *B04B 2005/0492* (2013.01)

(58) Field of Classification Search
CPC ............. A61M 60/113; A61M 1/3621; A61M 39/105; A61M 39/28; A61M 1/3696; A61M 39/12; A61M 1/3616; A61M 1/3606; A61M 1/029; A61M 1/0281; A61M 1/0272; A61M 1/0259; A61M 2039/0276; A61M 39/1011; A61M 39/10; A61M 1/303; A61M 1/3496; A61M 1/262; A61M 1/3639; A61M 1/30; A61M 1/26; A61M 1/308; A61M 1/0209; A61M 2039/226; A61M 1/285; A61M 1/16; A61M 1/14; A61M 1/3622; A61M 1/3623; A61M 1/03; A61M 494/01; A61M 494/07; A61M 494/08; A61M 494/11; A61M 494/22; A61M 494/84; A61M 494/02; F16L 37/56; G01N 33/491; C12M 47/00; C12M 47/02; C12M 47/04; C12M 23/26; C12M 37/04; C12M 27/10; C12M 25/06; C12M 23/28; C12M 33/10; C12M 29/00; C12N 5/0641; B04B 1/06; B04B 11/082; B04B 2005/0464; B04B 2005/0435; B04B 2005/0471; B04B 11/04; B04B 5/04; B04B 5/06; B04B 5/12; B04B 9/02; B04B 13/003; B04B 7/00; B04B 5/0442; B04B 2005/0478; B04B 2005/0492; B04B 13/00; B04B 9/10

See application file for complete search history.

(56) References Cited

U.S. PATENT DOCUMENTS

| | | | |
|---|---|---|---|
| 4,091,989 A * | 5/1978 | Schlutz | B04B 5/0442 494/45 |
| 4,113,173 A * | 9/1978 | Lolachi | A61M 1/3692 494/21 |
| 4,120,448 A * | 10/1978 | Cullis | B04B 5/0442 604/6.02 |
| 4,146,172 A * | 3/1979 | Cullis | B04B 5/0428 604/6.02 |
| 4,322,298 A | 3/1982 | Persidsky | |
| 4,636,193 A * | 1/1987 | Cullis | A61M 1/3696 494/45 |
| 4,776,964 A * | 10/1988 | Schoendorfer | A61M 1/3696 210/651 |
| 4,804,355 A * | 2/1989 | Brimhall | B04B 5/0421 494/20 |
| 4,850,995 A * | 7/1989 | Tie | A61M 1/3643 604/6.02 |
| 4,939,087 A * | 7/1990 | Van Wie | C12M 41/00 435/813 |
| 5,039,401 A * | 8/1991 | Columbus | B01L 3/5021 494/2 |
| 5,151,368 A * | 9/1992 | Brimhall | C12M 27/10 435/298.2 |
| 5,620,639 A * | 4/1997 | Stevens | A61M 5/158 264/572 |
| 6,192,568 B1 * | 2/2001 | Kafrawy | B29C 45/0055 29/430 |
| 6,423,023 B1 * | 7/2002 | Chang | A61M 1/3496 210/780 |
| 6,733,433 B1 * | 5/2004 | Fell | A61M 1/3698 494/56 |
| 9,248,446 B2 * | 2/2016 | Kolenbrander | A61M 1/3693 |
| 2011/0207225 A1 * | 8/2011 | Mehta | C12N 13/00 435/173.6 |
| 2013/0089917 A1 | 4/2013 | Kessler et al. | |
| 2014/0234829 A1 | 8/2014 | Ladtkow et al. | |
| 2015/0037882 A1 * | 2/2015 | Rowley | C12N 5/00 435/325 |

FOREIGN PATENT DOCUMENTS

| | | |
|---|---|---|
| WO | WO 2011/044237 A1 | 4/2011 |
| WO | WO 2014/070209 A1 | 5/2014 |

(56) References Cited

FOREIGN PATENT DOCUMENTS

WO    WO 2017/062176 A1    4/2017

OTHER PUBLICATIONS

International Search Report mailed Jul. 3, 2018 in International Application No. PCT/AU2018/050449, in 4 pages.
Written Opinion mailed Jul. 3, 2018 in International Application No. PCT/AU2018/050449, in 7 pages.
International Preliminary Report on Patentability mailed Apr. 8, 2019 in International Application No. PCT/AU2018/050449, in 5 pages.

* cited by examiner

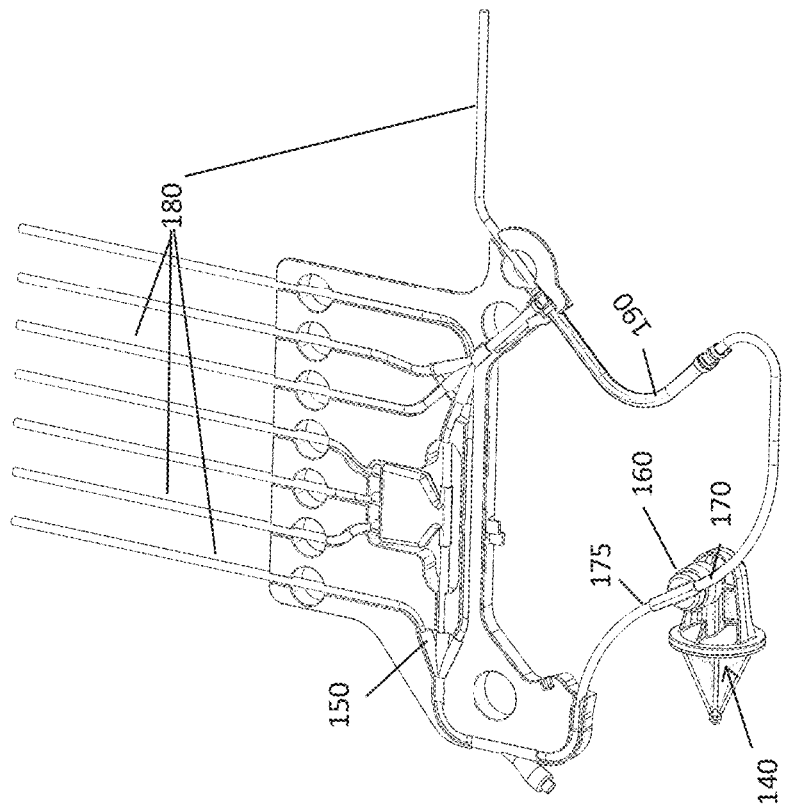
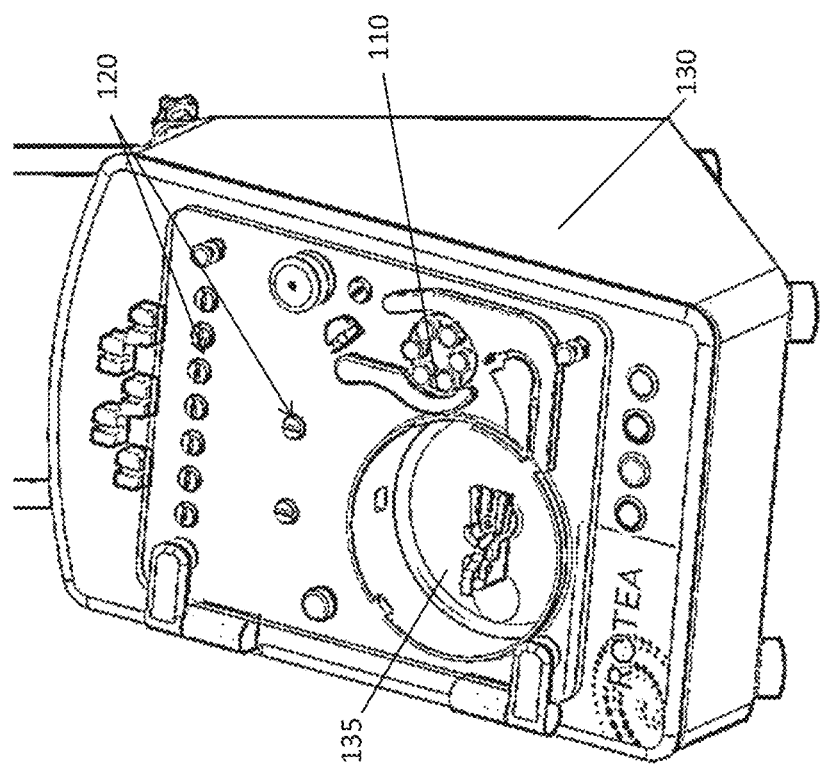
Figure 1d

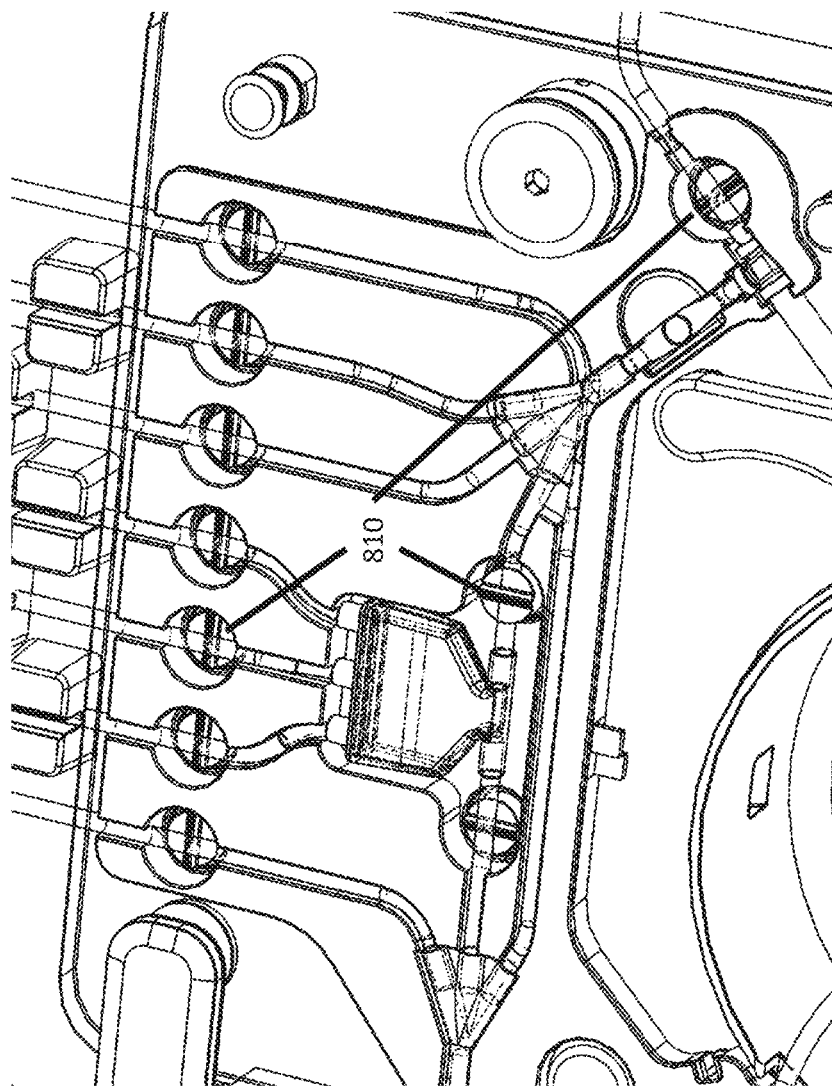

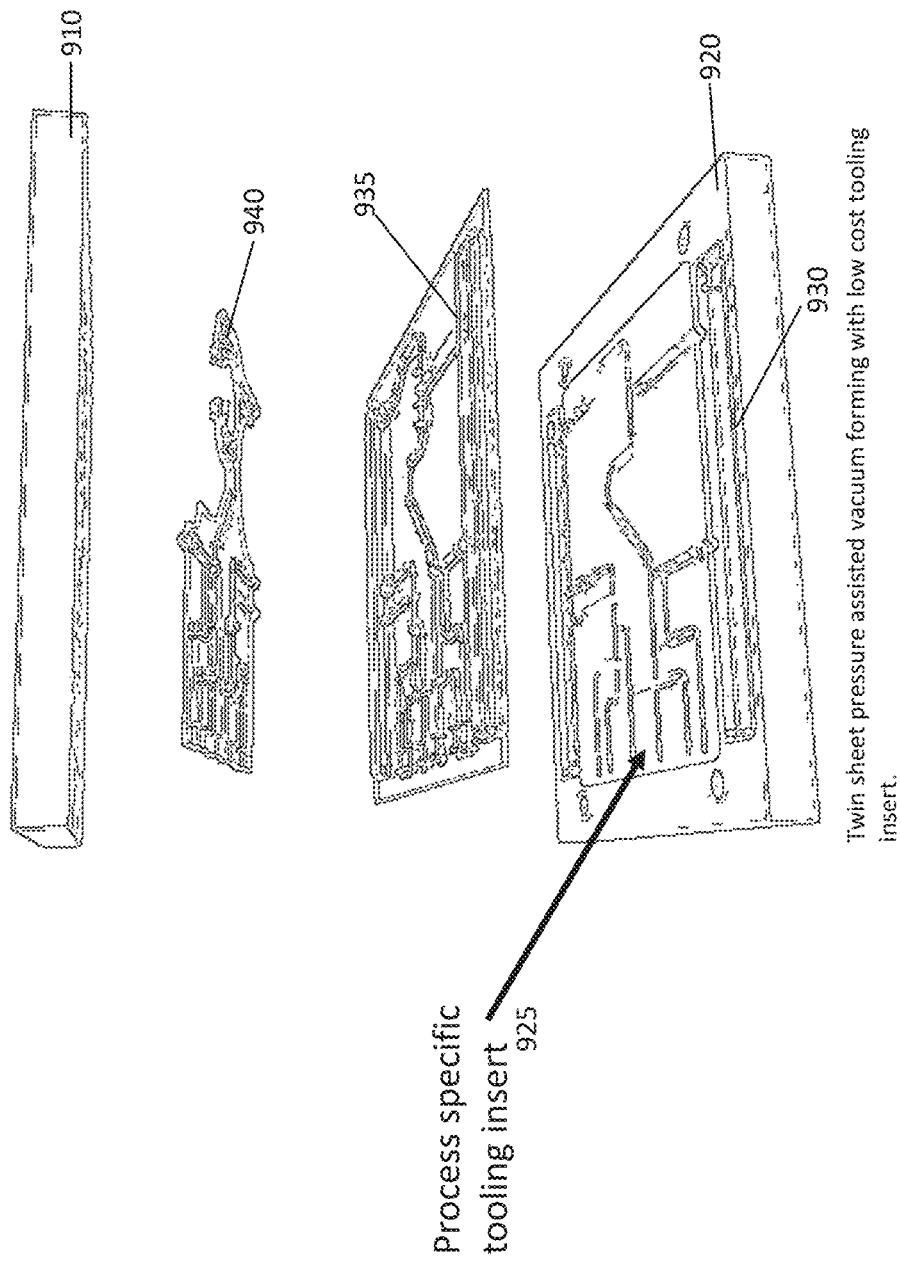

COMPACT REVERSE FLOW CENTRIFUGE SYSTEM

CROSS REFERENCE TO RELATED APPLICATIONS

The present application is a U.S. national phase application under 35 U.S.C. § 371 of International Application No. PCT/AU2018/050449, filed on May 11, 2018 and published as WO 2018/204992 A1 on Nov. 15, 2018, which claims priority to AU Application Nos. 2017901771, filed on May 12, 2017, and 2018900193, filed on Jan. 22, 2018. The content of each of these applications is incorporated herein by reference in its entirety.

TECHNICAL FIELD

The technical field of the invention is centrifuge apparatus for biological and other small particle separation applications.

BACKGROUND

Regenerative medicine and advanced cell therapies are emerging medical therapeutic technologies that build on manipulation of live, human derived cells to create constructs, deliver immunogenic responses or stimulate repair responses in the patient body. While some of these techniques can deliver many doses to multiple patients from a single source of cell (allogeneic products), there is growing recognition that processing and delivering cells derived from the patient or matched donor is safe and efficacious. To produce patient or matched donor specific cell products (autologous products) typically requires small batch processing.

To obtain regulatory approval, to make cell therapies widely available to patients, requires the equipment and process used to prepare the cell products be deemed safe and reliable, in addition to proving safety and efficacy of the particular therapy. A product specific, closed system has many benefits for cell product production. Such systems are designed for a dedicated function, i.e. a single production process for a specific cell product or set of cell products derived from the single production process. Such dedicated function closed systems are designed to deliver an aseptic processing environment for the medical product through close materials traceability and qualified sterilization protocols. Single use aseptic processing systems are assembled using a range of common disposable (one off use) components such as fluid bags and tubes etc. Assembly of these disposable system components can be complicated and time consuming.

Product specific systems designed for allogeneic products typically handle relatively large batches and may not readily scale to autologous products, where very small quantities of input and output products can be involved. There is a need for closed systems that can be used for production of small batch cell products for autologous cell therapies.

A typical step in producing the cell products used in cell therapies is washing and separation of the components of the cell products using centrifugation. Traditional centrifugation techniques require a vessel with the product to be manually transferred into and out of a separate centrifugation device. Accessing the vessel to add or remove product requires opening the vessel as an open process step or coupling and disconnecting it to an aseptic path. Reverse flow centrifugation with integrated fluid flow through the rotation system can be used to avoid these interactions.

Reverse flow centrifugation is a technique whereby the settling rate of particles in a fluid under centrifugal acceleration is counteracted by a flow of the supporting media. The particles are thereby suspended as a fluidized bed. Reverse flow centrifugation is so gentle that cells can be cultured, expanding in the fluidised bed state. Cell aggregation can be dramatically reduced. Further this technique enables separation of dead cell from live cells due to different density and morphology characteristics making reverse flow centrifugation the only currently available technology for increasing the viability of a cell population.

Delivering a fluid flow radial inwards to cells or particles under centrifugal acceleration creates a counter flow situation. The centrifugal acceleration experienced by each particle is proportional to the radial distance of that particle from the centre of rotation. To create a bed of fluidized particles the counteracting flow rate needs to be adjusted for each radius of rotation. This is achieved by shaping the chamber, commonly as a cone with the tip of the cone pointing radially outwards. The counter fluid flow is input through the cone tip. The fluid flow enters the tip of the cone at a relatively high velocity and the velocity of the fluid flow progressively reduces as it progresses radially inwards due to the increasing cross section of the cone. Historically there has been substantial investigation into chamber shapes and specific cone geometries for reverse flow centrifugation, much of this work is documented in the article by R. J. Sanderson, K. E. Bird, N. F. Palmer and J. Brenman: "Design Principles for a Counter Flow Centrifugation Cell Separation Chamber" Analytical Biochemistry 71, 615-622 (1976).

Reverse flow centrifugation has many benefits and is currently used in a number of commercially available dedicated function closed systems. However, the existing devices in the market are expensive to acquire as instruments. The disposable components kits for such systems are also typically high in cost. Operation of these devices can also be problematic as the disposable kits are often complex to load, introducing a high risk of human error and incorrect operation. Further, many of the currently available devices have limited flexibility in the protocol and kit configuration for application to novel cell product protocols.

Manufacturing complex medical products as a batch for each patient is creating demand for devices that can manipulate cell products within single-use functionally closed systems. Thus, there is a need for equipment that can be safely and reliably utilised for single use small batch processing to enable production of such patient specific cell products.

SUMMARY OF THE INVENTION

According to one aspect there is provided a compact reverse flow centrifuge system comprising:
  a reusable subsystem; and
  a single use, replaceable subsystem,
  the reusable subsystem comprising:
    a rotating motor head;
    a peristaltic pump;
    a valve assembly;
    a system controller configured to control operation of the rotating motor head, the peristaltic pump, and valve assembly in accordance with a programmed processing protocol; and
    case housing the rotating motor head, peristaltic pump, and valve operation assembly, and the single use, replaceable subsystem comprising:

a separation chamber configured for low fluid volume and small radius rotation, comprising a substantially conical fluid enclosure portion connected to a neck portion, and having a dip tube extending centrally through the conical fluid enclosure from the conical tip through the neck to provide a fluid path to the tip of the conical fluid enclosure, the neck portion further comprising an elution fluid path;

a fluid delivery manifold comprising a first fluid port and a second fluid port configured for fluid communication with the separation chamber, a plurality of fluid paths configured for connection to external fluid supply components for delivery of fluid to or from the first fluid port and the second fluid port at least one of the fluid paths being configured for engagement with the valve assembly whereby fluid paths can be selectively opened or closed by operation of the valve assembly, and a pump engagement portion configured to enable operable engagement between the peristaltic pump and fluid paths to cause fluid flow within the manifold by operation of the peristaltic pump; and a rotary coupling connecting the separation chamber to the fluid delivery manifold and providing a first fluid communication path between the dip tube and the first fluid port and a second fluid communication path between the elution fluid path and the second fluid port, the rotary coupling being configured to allow rotation of the separation chamber about a rotational axis relative to the fluid delivery manifold while the fluid delivery manifold is held in a fixed position by the case;

the neck portion being further configured to engage with the rotating motor head to cause rotation of the separation chamber about the rotational axis, the single use replaceable subsystem providing a closed environment for execution of reverse flow centrifugation processes.

In some embodiments the first fluid communication path from the dip tube to the first fluid port aligned with the axis of rotation through the rotary coupling. In an embodiment, the first fluid communication path may be provided by a tube through an axle of the rotary coupling.

In some embodiments the elution fluid path through the neck comprises at least one fluid path from the conical fluid enclosure to the elution path in the neck portion in fluid communication with the second fluid communication path through the rotary coupling.

In an embodiment the separation chamber includes a wall separating the conical fluid enclosure from the neck portion, the wall having one or more apertures formed therein to provide the at least one fluid path to the elution path in the neck.

Embodiments can further comprise a plurality of fluid paths from the elution fluid path in the neck portion through the rotary coupling in fluid communication with the second fluid communication path.

Embodiments of a compact reverse flow centrifuge system are provided wherein the tip of the conical fluid enclosure includes a fluid channelling structure is configured to cause dispersal of fluid introduced via the dip tube through the conical fluid enclosure. The fluid channelling structure can be further formed to hold the dip tube in an operational position.

In some embodiments the cone portion of the conical fluid enclosure has a unitary construction whereby joins in regions of maximum centrifugal acceleration are avoided.

Embodiments can be further configured wherein the valve assembly comprises a pinch valve actuation assembly comprising a plurality of pinch valve actuators, each pinch valve actuator configured to engage with a fluid path of the manifold and wherein the fluid delivery manifold includes at least one flexible portion in each fluid path aligned with one of the pinch valve actuator, whereby operation of the pinch valve actuators causes opening or closing of the fluid path.

In some embodiments the fluid delivery manifold is configured by actuation of valves and the attachment of vessels with suitable fluid connections to enable selective configuration of a recirculating fluid path for establishment of the fluidised bed in the chamber from the cell suspension supply vessel without risk of systematic cell losses.

In some embodiments the fluid delivery manifold is configured to align the pump engagement portion with the peristaltic pump when the manifold is positioned in the case and wherein the case is configured to effect operative engagement of the pump engagement portion with the peristaltic pump when the case is closed. For example, the case can be configured such that relative geometry of a case door and case door hinge gather a tube of the pump engagement portion into engagement with the peristaltic pump rollers to effect operative engagement with the peristaltic pump.

Embodiments can be configured for low rotation radius and high rotation speed operation.

In one embodiment the reverse flow centrifuge system is configured to operate at rotation speeds up to 8000 revolutions per minute. In this embodiment the conical fluid enclosure can have a volume of 5 ml to 20 ml. In an embodiment the conical fluid enclosure has a volume of 10 ml. The reverse flow centrifuge system can have a tip rotation radius of 50 to 70 mm. The axis to tip rotation radius can be 67 mm. In an embodiment the separation chamber has a cone diameter of 33 mm and cone height of 38 mm. An embodiment may be configured for use for cell therapies to enable fluid volume recoveries from 2 ml to 10 ml for with up to 10 million to 2 billion cells recovered within these volumes.

In another embodiment the compact reverse flow centrifuge system is configured to operate at rotation speeds up to 200,000 revolutions per minute. In this embodiment the conical fluid enclosure may have a volume of 0.1 ml to 0.5 ml. In an embodiment the conical fluid enclosure has a volume of 0.2 ml. In an embodiment the reverse flow centrifuge system has a tip rotation radius of 10 to 30 mm. This embodiment may be used to address concentration of exozomes (40-200 nm scale) and microvesicles (150-1000 nm scale). The microparticles are delivered directly to the settled region at the tip avoiding the long settling time required by ultracentrifugation.

Embodiments are also envisaged having fluid enclosure volumes in the range of 0.5 to 5 ml.

Embodiments are also envisaged having tip rotation radius in the range of 30 to 50 mm.

According to another aspect there is provided a separation chamber for a compact reverse flow centrifuge system, the separation chamber being configured for low fluid volume and small radius rotation and comprising:

a substantially conical fluid enclosure portion;

a neck portion connected to the substantially conical fluid enclosure portion;

a dip tube extending centrally through the conical fluid enclosure from the conical tip through the neck portion to provide a fluid path to the tip of the conical fluid enclosure;

an elution path through the neck portion; and a rotary coupling, connected to the neck portion, providing a first fluid communication path to the dip tube for fluid communication with a first fluid port for connection to a fluid delivery manifold, and a second fluid communication path to the elution fluid path for fluid communication with a second fluid port for connection to a fluid delivery manifold, the rotary coupling being configured to allow rotation of the separation chamber about a rotational axis;

the neck portion being further configured to engage with a rotating motor head to cause rotation of the separation chamber about the rotational axis.

The first fluid communication path can be from the dip tube to the first fluid port aligned with the axis of rotation through the rotary coupling. The first fluid communication path may be provided by a tube through an axle of the rotary coupling. The tube may form part of the axle in some embodiments.

In an embodiment the elution fluid path comprises at least one fluid path from the conical fluid enclosure to the elution path in the neck portion in fluid communication with the second fluid communication path through the rotary coupling.

In an embodiment the separation chamber includes a wall separating the conical fluid enclosure from the neck portion, the wall having one or more apertures formed therein to provide the one or more fluid paths to the elution path in the neck.

BRIEF DESCRIPTION OF THE DRAWINGS

An embodiment, incorporating all aspects of the invention, will now be described by way of example only with reference to the accompanying drawings in which

FIG. 1c shows an example of the assembled system components within the case for the embodiment of FIG. 1a;

FIG. 1d shows separately the reusable subsystem and a single use replaceable subsystem (kit) for the embodiment of FIG. 1b;

FIGS. 8a and 8b show examples of valve actuation assemblies for the Embodiments of the system shown in FIGS. 1a and 1b respectively;

FIG. 9 illustrates a manifold forming process;

DETAILED DESCRIPTION

Embodiments of the present invention provide a reverse flow centrifuge system configured for low fluid volume and small radius rotation. Embodiments of the system have applications for small scale processing with an automated protocol. An advantage of the low fluid volume and small radius of rotation is that the system can use high rotation speeds for increased processing speed for small batches. The system can be configured for bench-top operation or incorporated as a component of a more complex system. This can be advantageous for obtaining regulatory approval for medical products produced using the system. The process technology can be identically deployed in an integrated process for commercial manufacturing providing assurance of bioequivalence to regulatory investigators throughout clinical development. The system can provide a closed aseptic processing environment for medical products through use of materials traceability and qualified sterilization protocols.

Figure 1A:
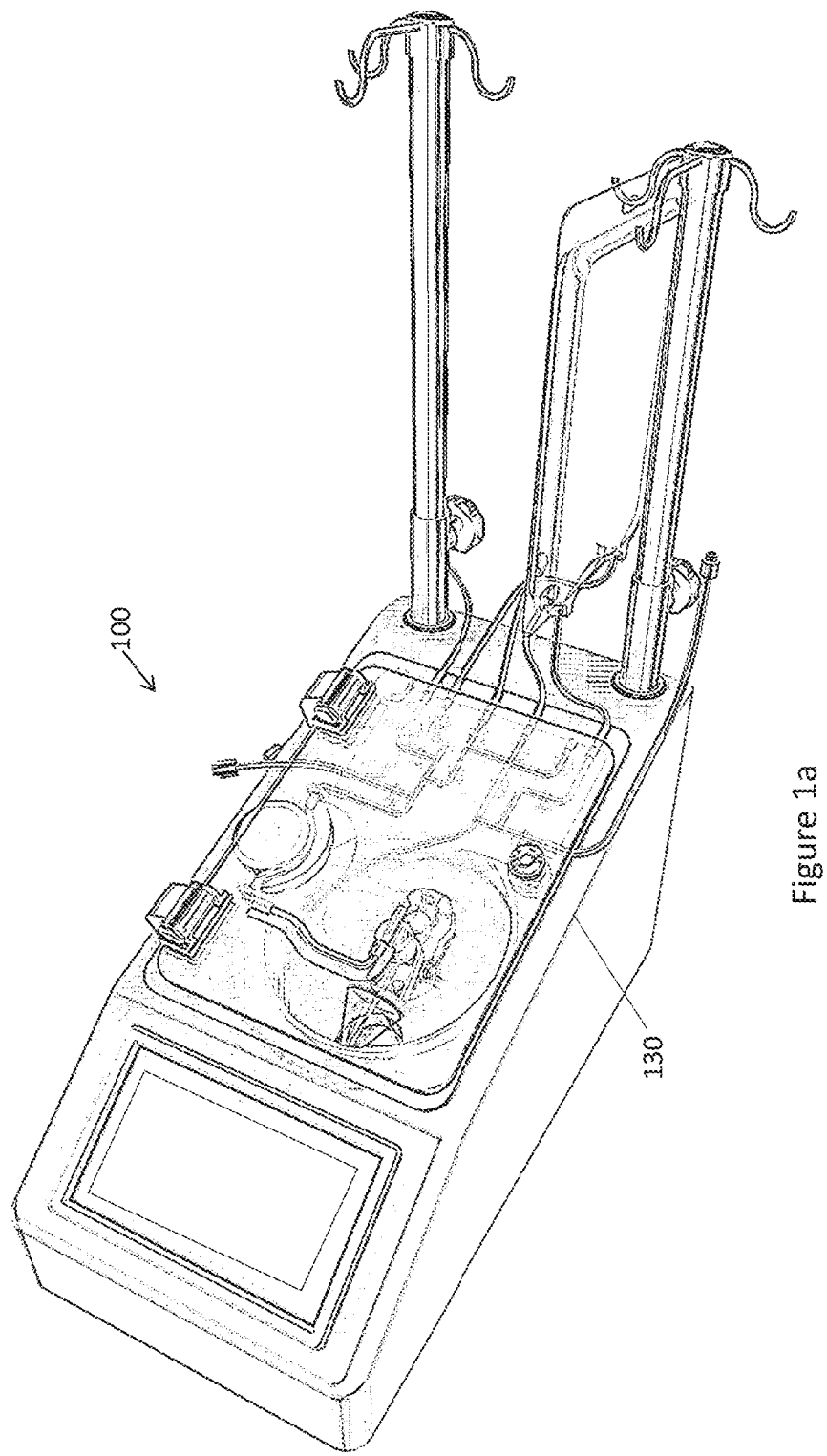
FIGS. 1a and 1b show examples of two alternative reverse flow centrifuge systems in accordance with embodiments of the present invention.
Figure 1B:
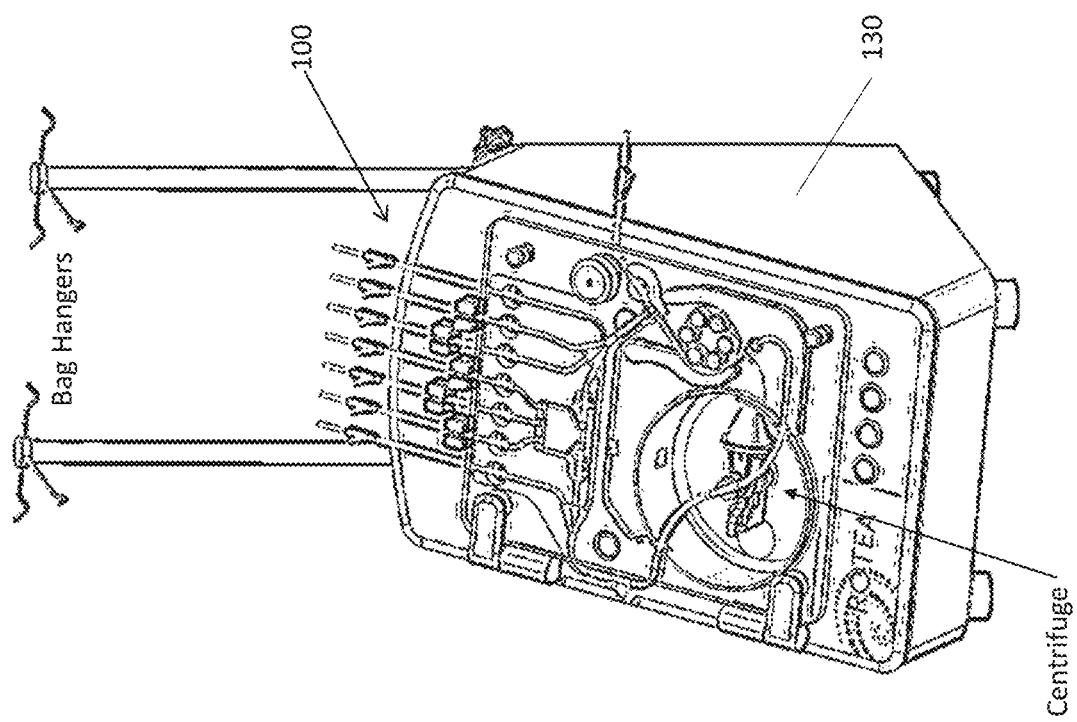
Figure 1C:
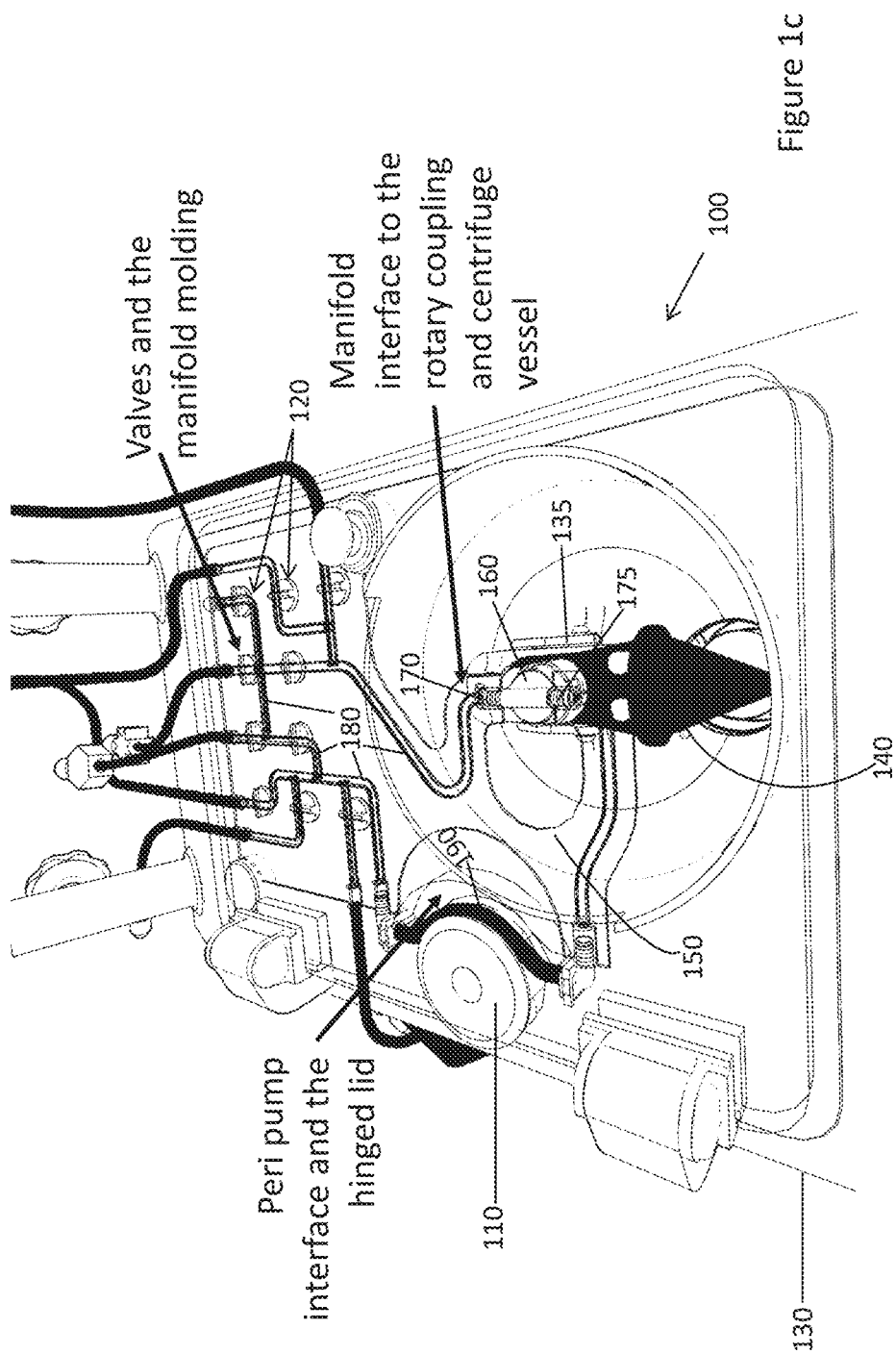

An embodiment of a compact reverse flow centrifuge system is illustrated in FIGS. 1a and 1b. FIG. 1c shows a view into a case housing the system components of the embodiment of FIG. 1a as assembled. FIG. 1d shows separately the reusable subsystem 1200 and single use kit 1205 for the embodiment of FIG. 1b. The same reference numerals have been used throughout FIGS. 1a to 1d. The system components are also illustrated in block diagram form in FIG. 12. The compact reverse flow centrifuge system 100 has a reusable subsystem 1200 and a single use replaceable subsystem 1205. The replaceable subsystem comprises disposable components which can be pre-assembled and sterilized for loading thereby simplifying loading protocols. Further pre-assembly can reduce risk of human error. This can also offer low operating costs by reducing the size and complexity of the disposable components compared with current commercial disposable component kits.

The reusable subsystem comprises a controller, a rotating motor head 135, a peristaltic pump 110 and valve assembly 120, a casing 130 houses these system components. The replaceable subsystem comprises a separation chamber 140, fluid delivery manifold 150 and rotary coupling 160 connecting the separation chamber 140 to the fluid manifold 150. The single use replaceable subsystem provides a closed environment for execution of reverse flow centrifugation processes.

Figure 2:
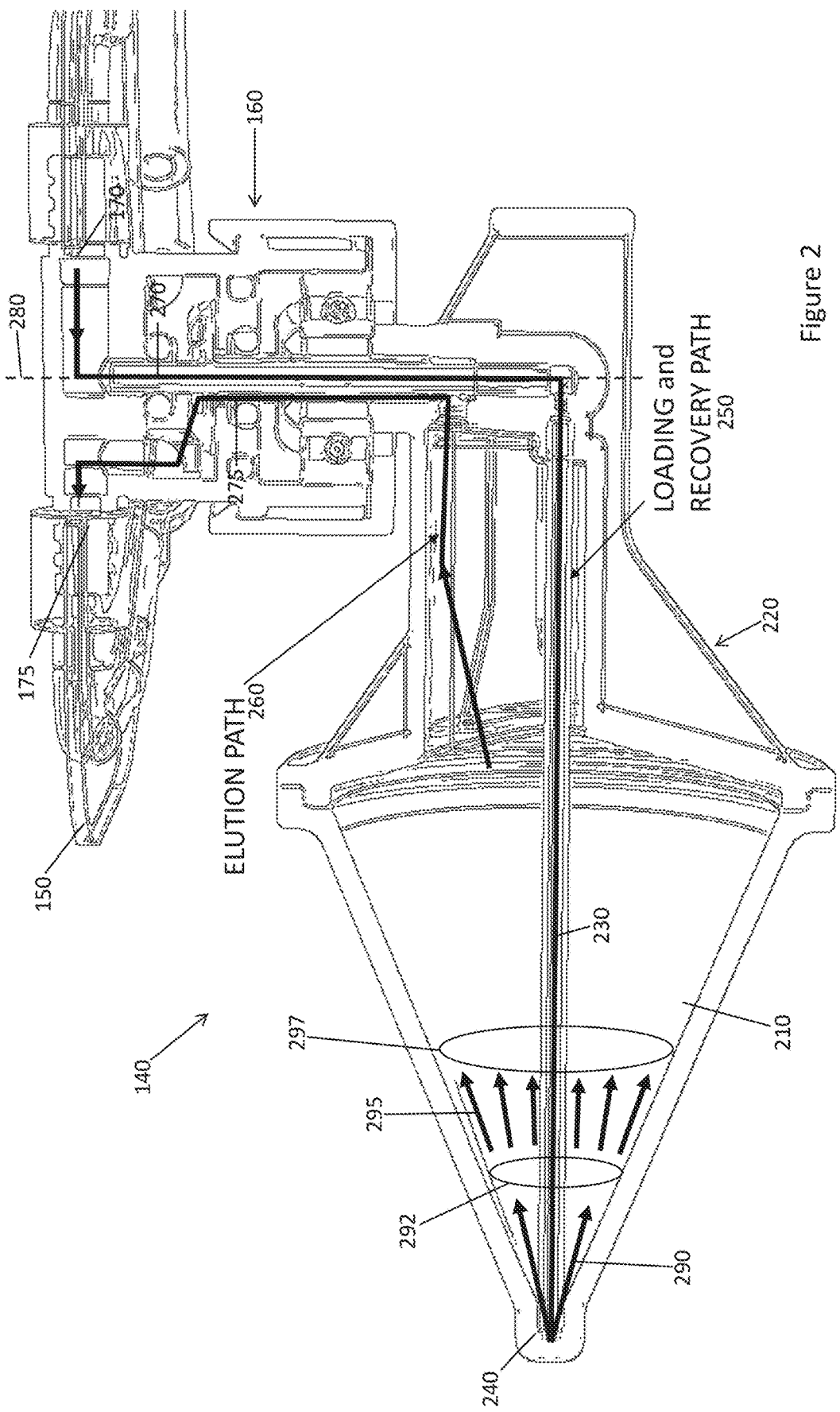
FIG. 2 shows an embodiment of the separation chamber.

The separation chamber 140 is configured for low fluid volume and small radius rotation. An example of an embodiment of the separation chamber is illustrated in FIG. 2. The separation chamber 140 has a substantially conical fluid enclosure portion 210 connected to a neck portion 220. A dip tube 230 extends centrally through the conical fluid enclosure 210 from the conical tip 240 through the neck 220 to provide a fluid path 250 to the conical tip 240 of the conical fluid enclosure 210. The neck portion 220 also includes an elution fluid path 260. The neck portion 220 is also configured to engage with the rotating motor head to cause rotation of the separation chamber about the rotational axis. The neck portion is also configured to engage with the motor head 135, which can also include a locking mechanism and be counter weighted to balance the separation chamber.

The fluid delivery manifold 150 comprises a first fluid port 170 and a second fluid port 175 configured for fluid communication with the separation chamber 140, and a plurality of fluid paths configured for connection to external fluid supply components 180 for delivery of fluid to or from the first fluid port 170 and the second fluid port 175. At least one of the fluid paths is configured for engagement with the valve assembly 120 for selective opening or closing by operation of the valve assembly. The manifold also includes a pump engagement portion 190 configured to enable operable engagement between the peristaltic pump 110 and fluid paths 180 to cause fluid flow within the manifold 150 by operation of the peristaltic pump 110.

A rotary coupling 160 connects the separation chamber 140 to the fluid delivery manifold 150. The rotary coupling is configured to allow rotation of the separation chamber 140 about a rotational axis relative to the fluid delivery manifold 150 while the fluid delivery manifold is held in a fixed position by the case 130. This rotary coupling 160 also provides a first fluid communication path 270 between the dip tube 230 and the first fluid port 170 and a second fluid communication path 275 between the elution fluid path 260 and the second fluid port 175.

An advantage of the system is that the same system components and processing functionality can be utilized in a laboratory type setup as for a fully scaled commercial production system.

The configuration of the separation chamber enables the small rotational radius and high rotation speed. An example of the separation chamber is shown in FIG. 2, the separation chamber 140 comprises a substantially conical fluid enclosure 210 and a neck portion 220. It should be appreciated that although the embodiment shown used a conical fluid enclosure 210, embodiments may not always use a perfect cone, some variation on this structure is contemplated within the scope of the present invention, for example a short straight sided portion may be used near the wide end of the cone or at the tip, alternatively a stepped conical structure maybe used. A dip tube 230 extends through the conical fluid enclosure 210 from the neck for delivery of fluid to the tip of the cone 240. An elution path 260 is provided through the neck 220 and rotary coupling 160.

It should be appreciated that by using an internal dip tube 230 is a significant divergence from commercial reverse flow centrifugation architecture, which provides a fluid path external to the separation chamber and the separation chamber has an inlet at the tip to supply the counter fluid flow to the separation chamber. The internal dip tube and rotary coupling enables reduction in size of the rotating components compared with previously known system which require external fluid paths to the chamber tip. This enables spinning at higher speeds creating higher centrifugal force than external fluid path systems, resulting in relatively high throughput for the chamber size. Thus, an advantage of the embodiments of the present separation chamber enables a single chamber to be used to process a typical batch size for autologous cell therapies. This can have benefits for reducing costs for providing such treatments. Further, being able to operate using higher centrifugal force also enables corresponding increases in flow rate operating ranges, thus increasing ability to optimise settings to isolate discrete cell types. Embodiments enable a wide range of centrifuge speeds and flow rates enabling selection of flow rate based on cell type.

The wide centrifuge speed range capability in one embodiment from 50 G's to 3000 G's (calculated at the radius corresponding to ⅓ of the cone height from the tip of the cone,) enables a wide range of flow rates. For example, a fluidized bed of cells stable at 5 ml per minute at 100 G's will exhibit similar bed stability at 150 ml/minute at 3000 G, thus enabling selection of any flow rate within this range to meet high process throughput objectives while enabling detailed fluid flow manipulations at low speed. By comparison known commercial counterflow centrifuge systems supporting single use kits offer centrifuge speed ranges up to 1,000 G's. The operating flow rate ranges are consequently limited in these commercial systems. The broad speed range enabled by embodiments of the described reverse flow centrifuge also facilitates differential cell type selection strategies that take advantage of the counter flow principles. One example is separation of viable cells from non-viable cells resulting in increased cell population viability, unique for counter flow centrifugation. A second example is the selective separation of red blood cells that are difficult to remove because their size and density creates an overlap to the selection criteria of most other cells within the operating envelope of other commercial systems. Taking advantage of the high speed centrifuge capability, the relatively dense but small cells can be retained in the fluidised bed while the larger peripheral blood mononuclear cells (PBMCs) of interest are eluted from the chamber.

Figure 3A:
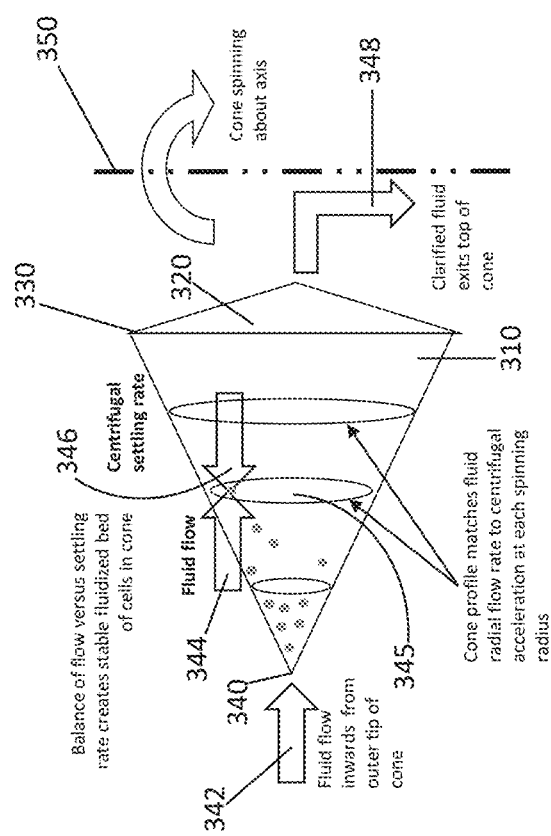
FIG. 3a illustrates the fundamental concepts of involved in a reverse flow centrifugation process.
Figure 3C:
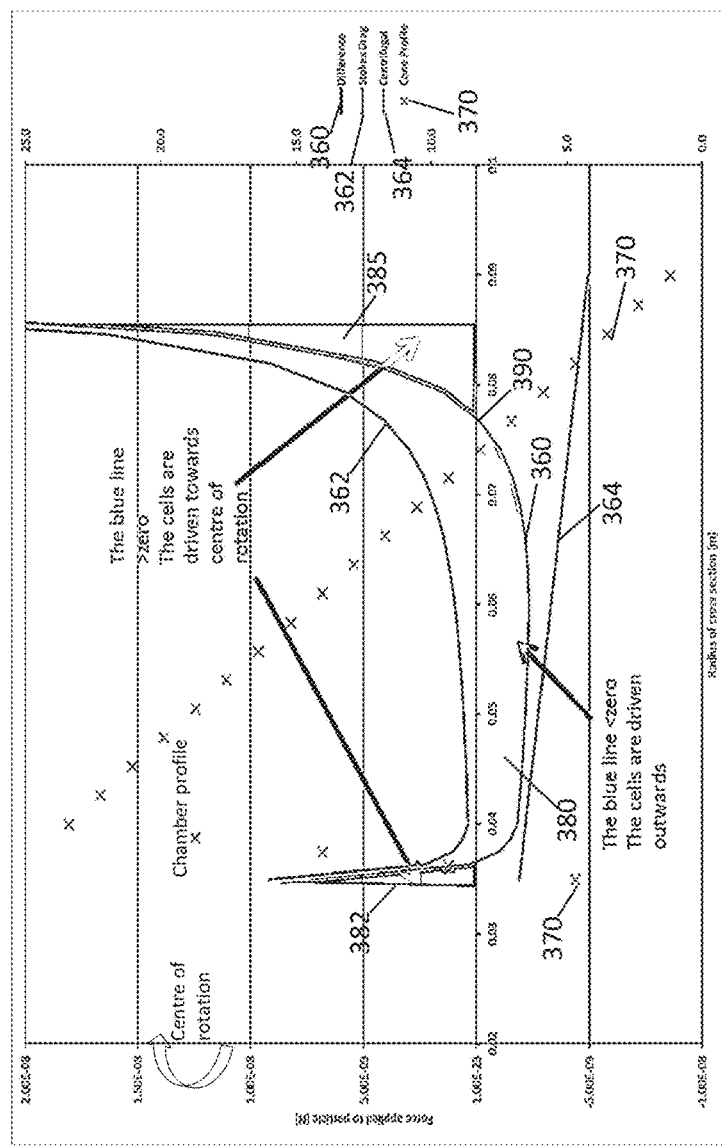
FIG. 3c shows the force applied to a particle for one particle size at one set pump (fluid delivery) speed and rotation speed.
Figure 3B:
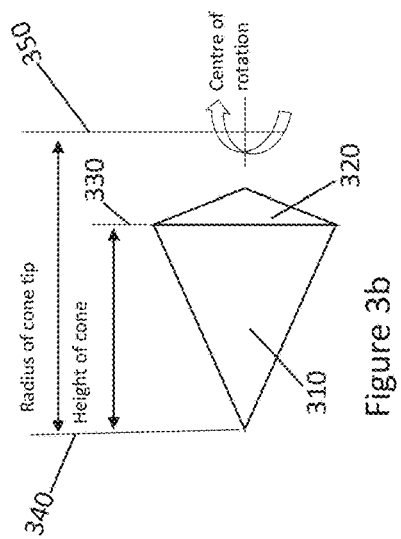
FIG. 3b diagrammatically illustrates key geometry features of the separation chamber.
Figure 3D:
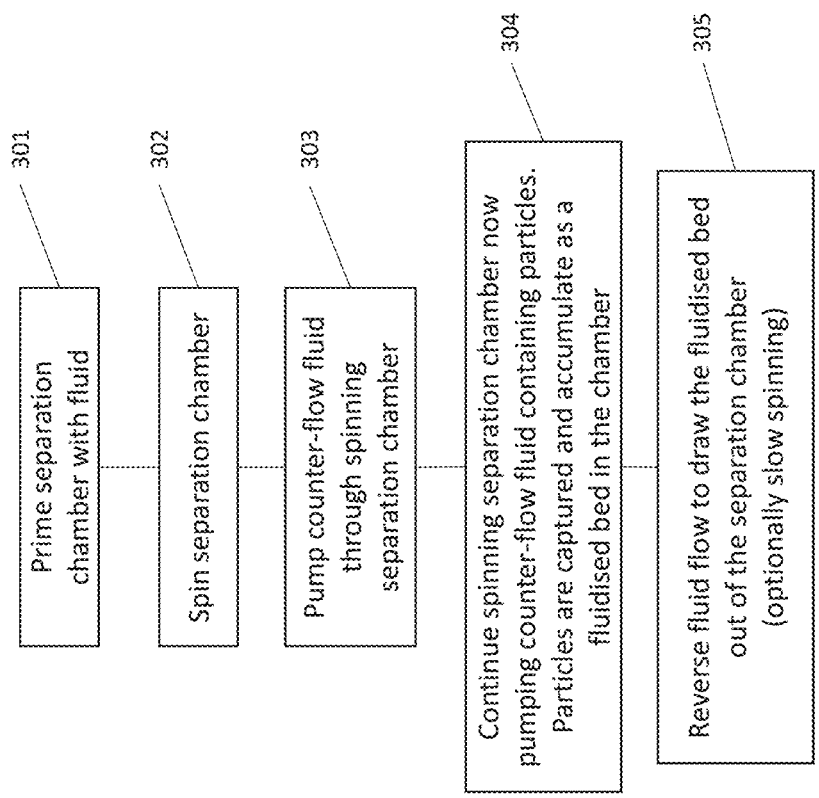
FIG. 3d is a flowchart of a simple example of a separation process using a reverse flow centrifuge.

FIG. 3a illustrates the fundamental concepts involved in a reverse flow centrifugation process, this will be discussed in the context of a process as shown in the flowchart of FIG. 3d concentrating a cell population suspended in the input fluid. In a first phase of the process 301 the rotating chamber and surrounding fluid lines are flooded with priming fluid. The chamber 310 is set spinning 302 around the axis 350 to create the centrifugal acceleration. The input fluid flow 342 containing the cells is now pumped 303 through the chamber. The speed of that pumped flow rate is selected so a fluidised bed of the cells will form as they enter through the tip of the cone 340. The fluid can be the original cell suspension fluid used for initial loading, thereby continuing to introduce cells into the chamber. The centrifugal acceleration will cause the cells to settle towards the outer end of the chamber 310, by adding the input fluid flow 342, 290 in the opposite direction to the direction of settling, the cells can be held suspended. The chamber is shaped so that the local fluid velocity 344, 295 is aligned to the centrifugal acceleration 346 at each radius 292, 297 to create a working zone 345. With the correct flow rate, fluid media and centrifuge speed, cells will accumulate in the working zone 345 and form a stable fluidized bed 304 in that zone. Cells entering the zone will form and join the fluidized bed in the working zone 345. It should be appreciated that as the cells are introduced to the chamber by the counter fluid flow 290, these cells will effectively be deposited at the fully settled point as they enter the chamber by the combined action of the fluid flow and centrifugal acceleration, so there is no "settling time" using this process.

An outlet allows this clarified fluid 348 to leave the chamber 310. It should be appreciated that the centrifuge speed, flow rate and fluid characteristics (i.e. density and viscosity) will support the cells being retained as a fluidised bed building from the tip of the cone. Other cells however may be eluted out of the chamber. In some cases large or dense cells can form a pseudo pellet at the tip of the cone due to the high speed processing, this can become a problem during high-speed processing if not properly managed. This problem can be managed by way of example using a processing protocol designed to perform a first processing pass, directed to accumulating and removing the heavy or dense materials, before the accumulation pass (or passes) for the target population. Testing of prototype embodiments has shown extremely high, (around 98%,) cell recovery yield is possible. Due to the high yields multiple processing (accumulation) passes are practical. Thus, processing protocols may be designed to perform multiple accumulation passes, having some directed to removal of waste and others for accumulation and recovery of target population(s).

Once the cells have been accumulated in the fluidised bed a recovery step 305 is used to retrieve the cells as a concentrate where the fluid flow direction 342 is reversed. The fluidised cell bed moves toward the tip 340 of the cone and drawn out of the cone, via the same fluid channel that was used for fluid input.

Reverse flow centrifugation can also be used to isolate different cell populations by virtue of their response to the conditions in the chamber. Increasing the reverse flow rate where a fluidised bed has been formed will result initially in the bed expanding, more intercellular space between each cell, the bed expanding up the cone. Some cells that may be smaller or have "rougher" external morphology may have a different settling velocity resulting in them being unstable in the fluidised bed and being driven out of the cone—inwards. The washing of cells out of the chamber in this way is described as elutriation which is a well known protocol for differential selection of cell populations.

The process experienced by cells within the spinning conical fluid enclosure 210 of this small device is identical to the process within larger implementations of reverse flow centrifugation. As a laboratory scale system for the development of live cell processes this system delivers the process identically without systematic scale effects. This is important for the development of formally regulated therapeutic products where, without the means to fully characterize a product as complex as populations of live cells the regulator's view is the "process is the product." There is a risk when changing the scale of a process that the process is different, making regulators suspicious that the product and its performance proven through clinical trials is different. Technically this system can deliver identical cell processing functionality for a laboratory scale system when incorporated into larger systems.

The conical fluid enclosure 210 has a small volume, yet through the benefits of reverse flow centrifugation it can support cell concentrations exceeding 100 million cells per ml enabling a single 10 ml chamber loading to support more than 1 Billion (1e9) cells that is sufficient for many therapeutic processes. These figures are dependent on cell size and more than 2 billion Chinese Hampster Ovary (CHO) cells have been processed in the 10 ml chamber with greater than 95% recovery by way of example. An embodiment that may support these cell concentrations can be around 10 ml in capacity. However, much smaller volumes may also be used as will be discussed further below.

The design has intentionally placed the conical fluid enclosure 210 at a small radius relative to the centre (axis) of rotation 280. This intentionally minimizes the kinetic energy in the rotating system relative to the centrifugal acceleration. Kinetic energy increases with the square of the radius and the square of the speed of rotation. The acceleration increases with the square of the speed of rotation but is linearly proportional to radius of rotation. This principle has been applied in embodiments of the system to successfully keep the kinetic energy at a low and safe level, for example, less than 20 joules at 5800 rpm. This has the advantage of further simplifying instrument and consumable design. This can also have advantages in production cost for disposable components. Further, embodiments may enable kinetic energy to be maintained below a regulation threshold for requiring formal (or higher level) device qualification. Again, this can have cost advantages. The small system size may also have usability advantages, is it is easier (and cheaper) to ship, store and move—the system can be easily portable. The small kit also means the instrument footprint is small, having benefits in minimising space required in lab or clean room environments. Further, the small kit size can also present significant long-term advantages in costs associated with manufacturing, shipping and storing consumable components.

The low spin radius and rotary coupling configuration enables high acceleration rates relative other known commercial reverse flow centrifuge systems. It should be appreciated that a "skip rope" configuration is used in other systems to ensure fluid path integrity. A rotary coupling may be regarded as an inferior solution to the "skip rope" configuration. However, the rotary coupling may enable higher speed operation and achieve satisfactory fluid path integrity. This can also have an advantage in reducing cell loss compared with conventional external counter flow fluid paths, this is due to avoiding flow path structures that may cause accumulation in sections (i.e. bends) of the counter flow fluid delivery path. Further, potential cell damage due to shear caused by a combination of centrifugal forces and inertial forces on fluid flow where the fluid path changes direction (bends) around the separation chamber is reduced, as the dip tube provides a straight flow path to the separation chamber tip.

An advantage of higher acceleration rates is enabling the cells to be stable in a fluidized bed with higher reverse flow rates. This enables higher throughput rates when harvesting cells from dilute suspensions into the fluidized bed. Other reverse flow centrifuge systems tackle throughput by providing multiple process chambers, up to 6 working in parallel. From a practical context the higher rotational speed enables larger volumes of cell suspension to be processed in a given time.

Another advantage associated with reduction in the overall size is minimisation of the entrapped volume within the system during processing. This enables processing of very small volumes with minimal losses. The system enables processing small input volumes and delivering an accurate, small volume concentrate output.

Processing very small numbers of cells can be the only option in autologous therapeutic applications where every cell is effectively priceless. Avoiding systematic losses of these cells to the process is critical. When a fluidised bed forms in the chamber tip, detail of the flow within the chamber is influenced by the bed. Before the bed forms, the flow within the chamber is strongly influenced by Coriolis flow artefacts. Under these conditions, cells entering the chamber can be swept through to the inner, elutriation port, without forming a bed. Common practise is to start capturing cells with a low flow rate to encourage bed formation before progressively increasing the flow rate.

With very small cell populations to be processed, 5 to 10 million cells for example, potential losses from this bed establishment period are not acceptable.

The combination of features contained in the design embodiment facilitates a unique flow configuration for establishment of the fluidised bed without systematic losses of these precious cells. Referencing FIG. 3e the flow is configured so the cell suspension, supplied in bag 395 is drawn into the cone through connection 396. The clarified fluid exiting the chamber 310 is then returned to the supply bag 395 via connection 397. Cells are recirculated in this way enabling the fluidised bed to establish and accumulate. Once the bed is established the outlet flow from the chamber 310 can be directed to the waste bag 398 by closing valve 393 and opening valve 399 until the cell suspension from the input bag has been drawn in.

Figure 3F:
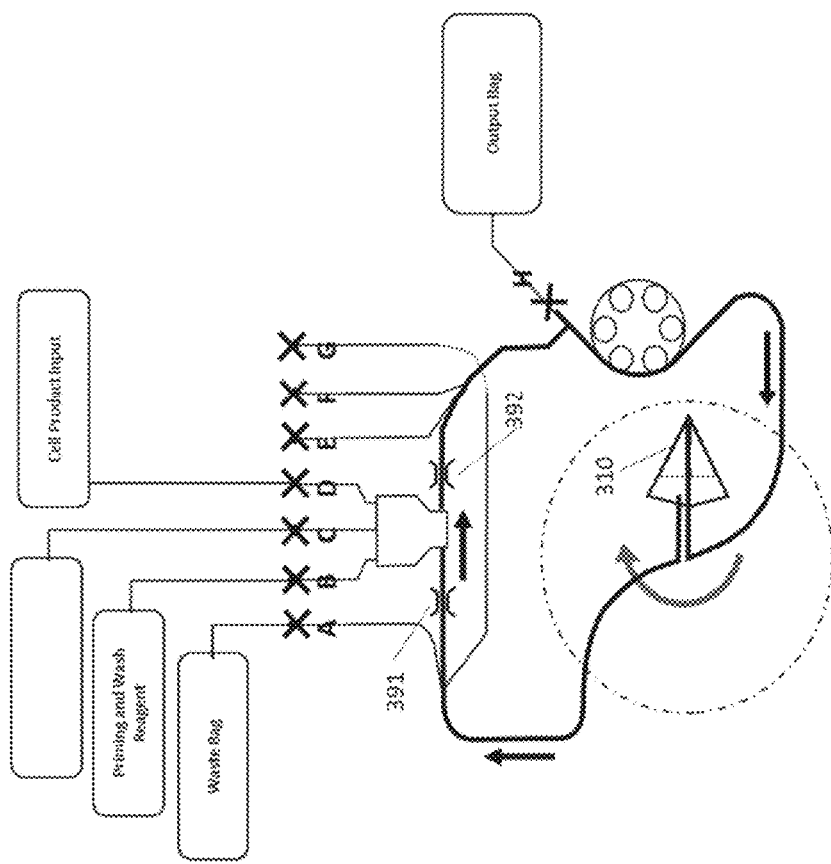
FIGS. 3e and 3f are diagrammatic representations of examples of system operation and fluid flow during processing.

Once the fluid suspension has been drawn in the fluid path can be re-configured by changing valves and pump configurations to proceed with the next step. One option is to enter a recirculation mode as illustrated in FIG. 3f where valves 391 and 392 are opened while all other valves are closed. The pump continues to flow the recirculating fluid through the chamber sustaining the cells in the fluidised bed state. A range of process strategies can be built around this proven recirculating operating state.

Key geometric features of an example of the substantially conical fluid chamber are abstracted in FIG. 3b, illustrating the cone 310 and neck connection 320 for the elution path (not shown), the base of the cone 330 is the widest part of the fluid chamber, and the centre of rotation 350 is indicated. FIG. 3b illustrates that the radius of the cone tip is measured from the centre of rotation 350 to the most distal point of the cone tip 340, and the height of the cone is measures from the base of the cone 330 to the cone tip 340. These radial distances are key for calculation of centrifugal acceleration (G force) experienced in the fluid medium for different rotational speeds. The details of the chamber shape can vary between embodiments and is a compromise. There is a family of chamber shapes that may be ideal depending on the details of the target particle and media used for processing. The chart shown in FIG. 3c shows the force applied to a particle for one particle size at one set pump (fluid delivery) speed and rotation speed. This graph shows the influence of chamber radius (x axis) on the forces applied to a particle (y axis). This graph shows that Stokes sedimentation 362 driven by centrifugal field 364 is balanced by the local opposing fluid flow (shown by the difference line 360). The shape of the cone 370 influences the fluid flow. In the zones 382, 385 where the differential force applied to the cell is positive, the cells will be driven towards the centre of rotation. In the zone 380 where the differential force on the cell is negative the cells will be driven outward. Looking at the cone profile 370 marked on the graph, the region 385 corresponds to a zone near the tip end of the cone, where the velocity of the incoming fluid is highest. The region 382 corresponds to the outlet from the chamber, where the fluid will be concentrated into the elution path. What will be observed in the chamber is accumulation of cells into a fluidised bed in the zone 380, a gap at the bottom of the cone corresponding to region 382, is the zone within the chamber where the cells will move towards accumulation in the fluidised bed, which will have a leading edge at the equilibrium point 390. The cells form a fluidized bed that creates a localized stabilizing influence.

A prototype embodiment of the chamber (using the configuration illustrated in FIG. 2) has a volume of 10 ml, a cone height of 38 mm and radius of 67 mm, this being measured from the centre of rotation 350 to the cone tip 340. In this embodiment the ratio of the cone height to the radius of the cone tip is 0.56. Prototype test results and calculation indicate this embodiment may be utilised with rotation speeds exceeding 7000 rpm or 3000 G at H/3, this is significantly higher than known commercial systems.

Common practice for assessing reverse flow centrifuge function is to describe the acceleration at ⅓ of the chamber height from the tip radius. This reflects the zone where the fluidised bed forms that in turn governs the fluid flow rate to balance cell settling rate. Embodiments of the present invention utilise a small chamber volume and small radius. Testing of a prototype embodiment has indicated that rotational speeds that may be achieved using a separation chamber as described with reference to FIGS. 2 and 3b can be at double or more the rotational speeds of currently available reverse flow centrifugation systems, and have significantly lower cone tip rotation speed for a rotation speed achieving 1000 G than that of the other devices.

As discussed above an advantage of the small radius the travelling speed of the tip portion of the cone is lower than for an embodiment having larger rotational radius rotating at the same speed. Thus, a smaller rotational radius can produce equivalent centrifugal acceleration to a target system using less kinetic energy. Alternatively, the smaller radius system can achieve greater chamber acceleration for the same kinetic energy as a larger system.

Another advantage enabled by a smaller rotational radius is increase in flow rate for the counter flow fluid. Equilibrium and establishment of the fluidised bed is achieved where the relative centrifugal acceleration Ca is balanced by the velocity of the counter fluid flow Fv. Considering gravitational effects are negligible at the rotational speeds in question, the equilibrium can be characterised by Equation 1:

$$Ca = w^2 R = \frac{Fr}{\pi r^2} = Fv \quad \text{[Equation 1]}$$

where w (rad/s) is the centrifuge velocity, R (mm) is the radial distance for the axis of rotation, Fr (ml/s) is the input fluid flow rate, and r (mm) the cone radius at the radial distance R. In the context of the generation of a fluidised bed r can be treated as a constant, so from Equation 1 it is apparent that for a smaller separation chamber as the rotational speed increases (w), higher input flow rate Fr is required to achieve equilibrium and establish the fluidised bed.

Typically the processing time for establishing the fluidised bed of cells and cell recovery is dependent on the flow rate. As discussed above the ability to use smaller rotational radius and greater rotation speeds, requires increased flow rate for the counter flow fluid which, in turn, can result in faster processing time. The ability to work with higher flow rates can avoid the need for multiple process chambers by enabling a protocol that has time constraints to be completed with the one small system. For example, harvesting cell product from multiple cell culture "factories" involves processing of 10's of litres of product. A system embodiment utilising the separation chamber design discussed with reference to FIG. 3 can have the capacity to process this volume more quickly than all but the large scale systems. A further advantage of using increased rotation speed and flow rates is this can also improve the stability of the fluidised bed during cell recovery, enabling high recovery rates.

Applying this principle to consideration of further smaller scale embodiments, an alternative embodiment may be configured with a smaller separation chamber for separation of exozomes that are in the 40 to 200 nanometre scale. Such an embodiment would operate at around 100,000 rpm, compared with around 8,000 rpm for a 10 ml system as illustrated in FIG. 3. The design principle being applied is to enable very high speed rotation by utilising a very low rotational radius. It is envisaged that embodiments may be implemented having rotation speeds up to 200,000 rpm. For example, a theoretical model indicates that the conditions to create a fluidised bed of 200 nanometer exozomes may be achieved using a chamber having a tip radius of 20 mm, cone length of 10 mm and rotational speed of around 100,000 rpm delivering 200,000 G at H/3 with a processing rate of 5 ml per hour. It is envisaged that such characteristics may be achieved using a scaled version of the present chamber configuration. As discussed above an advantage of the reverse flow centrifuge technique is minimal settling as particles are effectively introduced directly to their settled position by the counter fluid flow. An advantage of this is the time for the separation processing becomes dependent on the time required for introduction of the cells/particles to the settling chamber via the counter fluid. Therefore the processing time is dependent on fluid flow rate and particle concentration in the counter fluid, rather than specific particle type settling characteristics. For separation of particles such as exozomes this may be a very significant advantage. There is currently no reverse flow centrifuge system available for exozomes. Current state of the art for separating exozomes uses ultracentrifugation requiring hours of spinning to settle the particles.

A concern associated with the small separation chamber radius of rotation is the influence of Coriolis forces on the cells and fluidized cell bed. Coriolis forces are inertial and arise when there is flow in a radial direction within a rotating environment. This effect can be observed within the fluid chamber when viewed or recorded under stroboscopic illumination. The Coriolis effect can be observed as a tail of cell product being drawn up the leading edge of the fluid chamber. This tail quickly diminishes once the fluidized bed is established. The shape of the bed reflects the Coriolis reaction. Concern has been expressed that this behaviour will result in increased systematic cell losses if the chamber is located close to the centre of rotation. However, analysis by the inventors has indicated that the ratio of the Coriolis force to the centrifugal force is not affected by the radius of rotation, and the Coriolis force as a ratio of the centrifugal force reduces with increasing rotational speed. Analysis of the physics shows that the ratio of Coriolis force to centrifugal force acting on a particle in the cone is 2/w where w is the speed of rotation.

The fictitious forces action on a particle in the chamber can be characterised by:

$$F_{fict} = -2m\Omega \times v_R - m\Omega \times (\Omega \times R) - m\frac{d\Omega}{dt} \times R \qquad \text{[Equation 2]}$$

Where m is the particle mass, R is the radial distance, $\Omega$ the angular velocity vector ($\Omega = |w|\vec{\Omega}$) for the chamber having a magnitude equal to the rotation rate w, and $v_R$ is the velocity of the particle with respect to the rotating system at radial distance R. In Equation 2 the Coriolis force component is characterised by $(-2m\Omega \times v_R)$, the Centrifugal force component is characterised by $(-m\Omega \times (\Omega \times R))$, which can also be characterised $mw^2R(t)$ where R(t) is the instantaneous position vector of the particle, and the Euler component $$\left(-m\frac{d\Omega}{dt} \times R\right)$$

characterises force due to changing speed of rotation. Considering operation at a constant rotational speed, the Euler component may be ignored.

Looking at the comparative influence of the Coriolis force:

$$\frac{\text{Coreolis force}}{\text{Centrifugal force}} = \frac{(-2m\Omega \times v_R)}{(-m\Omega \times (\Omega \times R))} = \frac{2mwR(t)}{mw^2R(t)} = \frac{2w}{w^2} \qquad \text{[Equation 3]}$$

during reverse flow centrifugation the particle velocity relative to the rotating system $v_R$ is equivalent to the tangential speed of rotation of the chamber, and therefore particle position vector R(t). This indicates that the Coriolis force is independent of the rotational radius of the system. Further, that the relative influence of Coriolis force decreases with increasing rotational speed. The Coriolis force is influenced by the input flow rate and cone geometry, not the tip radius R. It should be appreciated that a constant rotational speed a constant input flow rate will be used during the settling (fluidized bed accumulation) process phase. Based on Equation 1, it should be appreciated that as the separation chamber tip radius R is made smaller the chamber size may also be made smaller, and the rotational speed increases. With a reduction in separation chamber size and volume (reduction in tip radius R), the cross sectional area of the cone will also reduce further diminishing the impact of the Coriolis force.

This means that the relative influence of the Coriolis effect diminishes with increasing rotational speed and is independent of the radius. The design embodied by this invention therefore presents an improved configuration for reverse flow designs and suggests this approach can be applied to applications where very high accelerations are needed for fine particle aggregation.

The single use separation chamber and support structure embodies the application of a range of physical principles to provide a component that may be economically produced for one off use.

In an embodiment the separation chamber fundamental configuration is to join a simple conical chamber component to a chassis structure that provides ergonomic, fluidic and structural interfaces. This structure uses a cone having a unitary structure which is then joined at the wide end to the supporting chassis forming the neck portion. This places the most radially outward joint at the base of the cone, relatively close to the axis of rotation (compared with the cone tip) and thereby at a point along the separation chamber where relatively low centrifugal acceleration is experienced compared with the cone tip. This configuration also avoids joins being at locations where high fluid pressure is experienced. For example, the cone tip will typically experience the highest fluid pressure. Thus, the unitary cone tip avoids joins in this high fluid pressure region.

Analysis of the pressure inside the spinning cone estimates a hydraulic pressure of 61 psi (4.2 BAR) at 1000 G's operating speed. The operational acceleration is calculated ⅓ of the cone height in from the cone tip spinning radius since that is where the fluidized bed is forming and active, at 2000 G the cone tip pressure is estimated at 8.4 bar. The compact geometry can be highly beneficial for reducing interior chamber pressure, for example, the pressure at the tip of the cone P=row×w^2×R^2/2 where row is the fluid density, R the rotational radius (distance to the rotational axis) and w the rotation speed. The fluid has a pathway to the centre of rotation so the pressure represents a fluid column of the full radius subjected to centrifugal acceleration—progressively increasing G force with radius. Creating the target G force at a low radius creates a lower internal pressure proportional to the rotational radius.

By avoiding structural joints in the tip region of the monolithic chamber design the product is substantially less exposed to manufacturing variances than other products. The joint required to connect the cone to the chassis is only required to support the mass loading from the cone structure supporting the mass of fluid it contains. This is a worst case load in the range of 500 Newton at 8000 rpm representing 3900 G versus the common working speed of 7000 RPM or 3000 G at the working height for the embodiment discussed with reference to FIG. 3.

This separation chamber design uses an internal straw (also referred to as a dip tube) for the fluid connection to the tip of the cone. This delivers a range of significant benefits:

No external fluid connection to the high-pressure region of the cone eliminating manufacturing and handling risks associated with the external plumbing configuration.

The fluid flow pattern of cell suspensions entering the fluid chamber is not influenced by geometry of the external plumbing that is required to turn back on itself to align to the conical chamber geometry.

External fluid lines and associated u-bends results in the highest centrifugal zone occurring outside the separation chamber. Heavy particulates and cell aggregates accumulate in the highest centrifugal zone. In known commercial systems this highest centrifugal zone occurs outside the separation chamber, for example in a bend in external plumbing near the fluid input at the tip of the separation chamber. In embodiments of the present invention this critical highest centrifugal zone is within the tip of the cone. Where the cone is transparent this highest centrifugal zone can also be clearly observed for managed intervention.

The central dip tube in the cone can be created from hypodermic tubing that is technically precise, approved for medicinal product contact and manufactured in sufficient volume to be low in cost. Hypodermic tubing is also a well-known component of the hazardous waste stream for these products after use. This can have advantages both for initial production cost and waste disposal costs for the separation chamber component.

The dip tube design in combination with features in the cone moulding can create well controlled reproducible fluid flow geometry in the fluid chamber. For example, using an interference fit between the dip tube and the chassis components, assembly tolerances between the tube cut length moulding features and cone joining are eliminated by axial re-positioning of the tube through the virtue of the interference fit. Embodiments of a fluid channelling structure formed in the tip of the separation chamber are illustrated in FIGS. 4a to 4f. The tip 400 of the conical fluid enclosure includes a channelling structure with a central portion 420 for receiving the fluid output from the dip tube 410 and lobes 430 spaced around the central portion to disperse the fluid flow around the conical fluid enclosure. The fluid channelling structure can also be configured to assist in locating and supporting the dip tube 410. For example, as shown in FIGS. 4b and 4f, the central portion 420 is sized to receive the end of the dip tube 410, which is be held in place by the interference fit and reinforced by the centrifugal force (shown in FIGS. 4c and 4f). In this embodiment the central portion 420 includes ledges 440 between the lobes 430 to control the dip tube axial location and ensure a consistent open fluid communication pathway between the dip tube 410 and the fluid chamber. Fluid from the dip tube enters the central portion 420 and flows out via the lobes 430 which provide the opening to the fluid enclosure. The embodiment shown uses three lobes evenly spaced around the tip, however, other structures may be use, for example, 4 or more lobes, or a plurality of evenly spaced radial channels. It should be appreciated that such a structure may simplify device manufacturing and assembly, in particular by reducing the precision required during the assembly process to ensure correct placement of the dip tube 410.

Fluid can be recovered from the chamber by reversing the fluid flow to draw the fluidised bed (i.e. concentrated cells) out through the dip tube 410. It should be appreciated that it is desirable to draw the fluidised bed out of the cone with minimal disturbance to the media environment the cells are suspended in and minimising dilution during the recovery process. The process conditions within the bed are controlled by centrifuge speed and fluid flow rate. Similar fluidised bed conditions can be created at a range of speeds by matching the flow rate. This allows the centrifuge rotation speed and fluid flow rate to be slowed as a coordinated action (for example controlled by the microprocessor controller) retaining the fluidised bed in a stable condition but at a slower process rate creating more favourable conditions for the recovery process. The limit to fluidized bed concentration is ultimately avoidance of blocking of the fluid path during the recovery step. The density of the fluidised bed can be adjusted by the counter flow pump before the recovery step enabling optimisation of the suspension concentrate. Counter flow centrifuge processing rate is defined by the centrifuge speed in combination with the counter flow pump rate. The processing rate can be slowed as a coordinated action before the recovery step to minimise risk of cell damage or cell loss from the chamber. This coordinated slowing involves controlled slowing of the centrifuge speed and counter flow pump rate.

Figure 4:
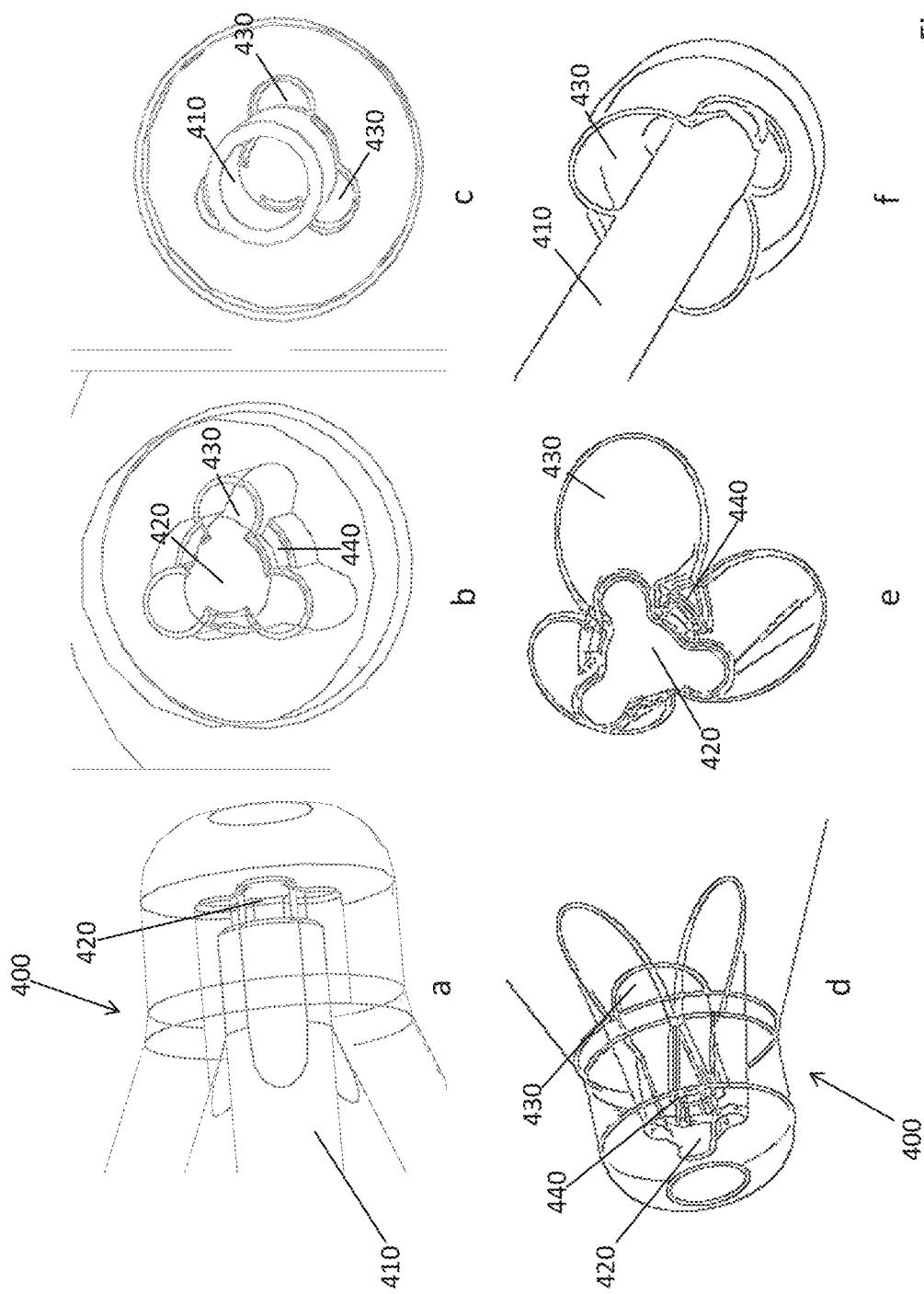
FIGS. 4a to 4f illustrates an embodiment of a fluid channelling structure formed in the tip of the separation chamber.

Slowing centrifugal rotation and flow rate may also reduce risk of cell damage during the recovery process. To maximise concentrated fluid recovery it is also desirable to have a very small gap between the dip tube and the end of the cone tip to reduce the amount of cell free fluid that may be drawn into the dip tube with the last of the fluidised bed, and reduce dilution towards the end of the fluidised bed recovery. The structure of the cone tip 400 can be designed to minimise the gap for good recovery outcomes. It should be appreciated that the channelling structure for supporting the dip tube as shown in FIG. 4 can be advantageous as the supporting ledge 440 and lobe 430 structure reduces the access area around the dip tube entrance for cell free liquid behind the fluidised bed. The central portion should be fully occupied by the fluid of the fluidised bed until the last moments of the fluidised bed being drawn out of the tube. Provided the flow rate is controlled to maintain stability of the fluidised bed the lobes should funnel all of the concentrated fluid to the dip tube ahead of the trailing cell free fluid to minimise dilution.

Many bioprocess specialists are concerned to ensure live cells are not exposed to excessive shear in the fluid environment. Shear can result in cell loss or damage during the production process effectively reducing the production process yield. It is desirable to avoid high fluid shear, however shear can occur in any system where inertial forces will be experienced during fluid channelling. A major attribute of the reverse flow centrifugation process is that it can deliver outstanding cell recoveries (>98%) of the introduced cell population being captured in the fluidized bed for recovery from the separation chamber. Therefore any systematic loss of cells after separation is a concern.

A feature of embodiments of this system is the use of a rotary coupling between the rotating centrifuge and the external fluidic system. Many existing reverse flow centrifuge products use a skip rope device that achieves this rotating connection without use of sliding seals. However, such a device can be complex and increase production costs. In embodiments of the present system a rotary coupling is used for simplicity and potential cost reduction. Further verification of a rotary coupling as a functionally closed biological device is required for commercial production and the regulatory validation protocols are well established for such devices as many other products accepted in the bioprocessing space use rotary couplings. This may also have an advantage in reduced regulatory approval costs, which may also impact positively on product costs. Using a rotary coupling can also enable higher rotational speeds than alternative "skip rope" type coupling designs.

Experience has demonstrated that poorly configured rotary couplings can impact cell recoveries. A range of design considerations have been employed in this embodiment to address points where cells may experience a high fluid shear situation. The design considerations in this patent embody several principals.

The fluid channel that connects to the dip tube is where a dilute cell suspension is transferred to the chamber during cell bed accumulation.

This channel is also where the concentrated suspension is drawn out of the chamber to the destination vessel.

The rotary coupling has a central port directly aligned to the centre of the rotating assembly to transmit the cell suspension.

The cells are therefore only exposed to shear from de-rotation as they emerge from the rotating structure into the rotary coupling body.

Figure 5:
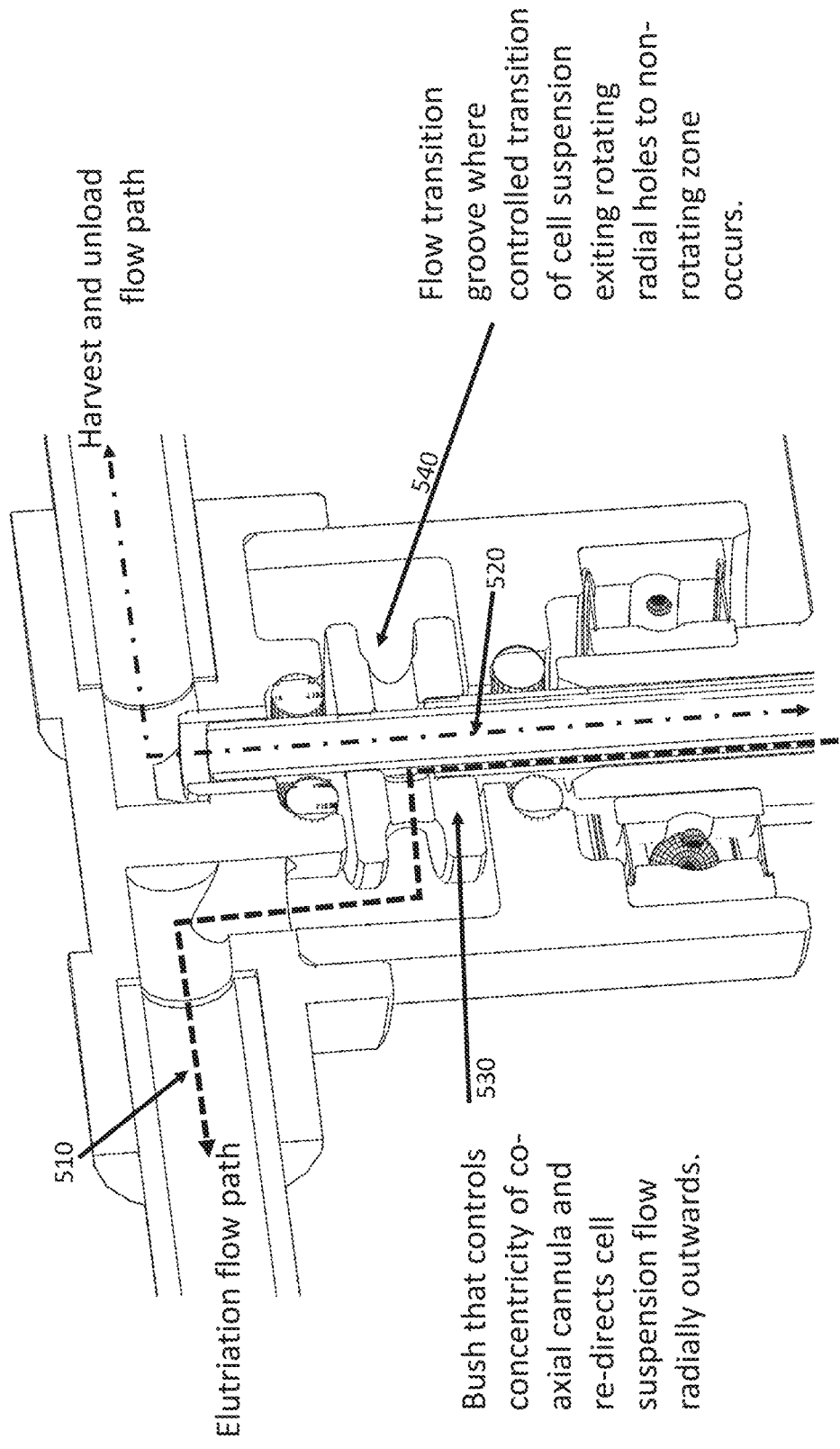
FIG. 5 shows an embodiment of the rotary coupling.

An embodiment of the rotary coupling and flow paths is illustrated in FIG. 2 and FIG. 5, which show the rotary coupling in more detail. The fluid channel 520 for the first communication path 270 communicating with the dip tube for loading and recovery 250 is aligned with the rotational axis. Thus, the fluid channel 520 for cell recovery of the concentrated cell suspension is located where the cells will experience the least possible shear stress when transferring out of the rotating environment.

The elutriation flow path 510 is through a coaxial cannula to the loading and recovery channel 520 and a flow transition grove 540 in a bush 530 of the rotary coupling. The Bush 530 controls concentricity of the coaxial cannula and re-directs cell suspension flow radially outward. The bush 530 has an annular flow transition groove where controlled transition of the cell suspension exiting rotating radial holes to the non-rotating zone occurs. The fluid flow from the inner, large diameter, end of the conical fluid enclosure 210 is commonly clarified media with no cell population, destined for waste. It is logically this channel where the fluid must move radially outwards and stop rotating before exiting the rotary coupling. The elutriation flow path 510 through the coaxial cannula is however used in a range of applications where cells are selectively driven out of the fluidized bed (elutriation), or the entire cell bed is mobilized through a recirculation loop for mixing and sampling.

Embodiments employ a flow transition groove 540 that directs the fluid (and any cells in it) to move radially outward in a generous shared volume before being directed to merge at the rotary coupling outlet. Details in the moulded components within the coupling are designed to minimise dead flow zones where cells can accumulate and be lost.

Figure 6:
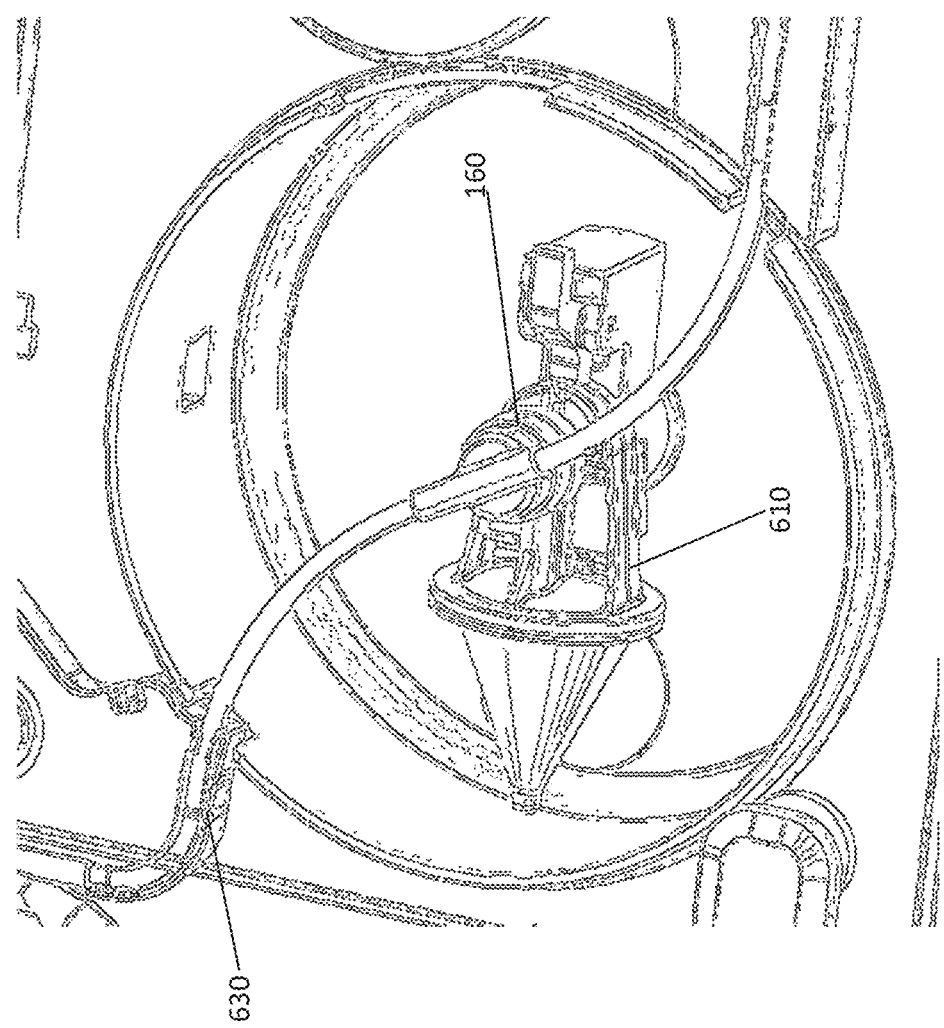
FIG. 6 shows an example of the separation chamber and manifold in an operable position in the reverse flow centrifuge case.
Figure 7:
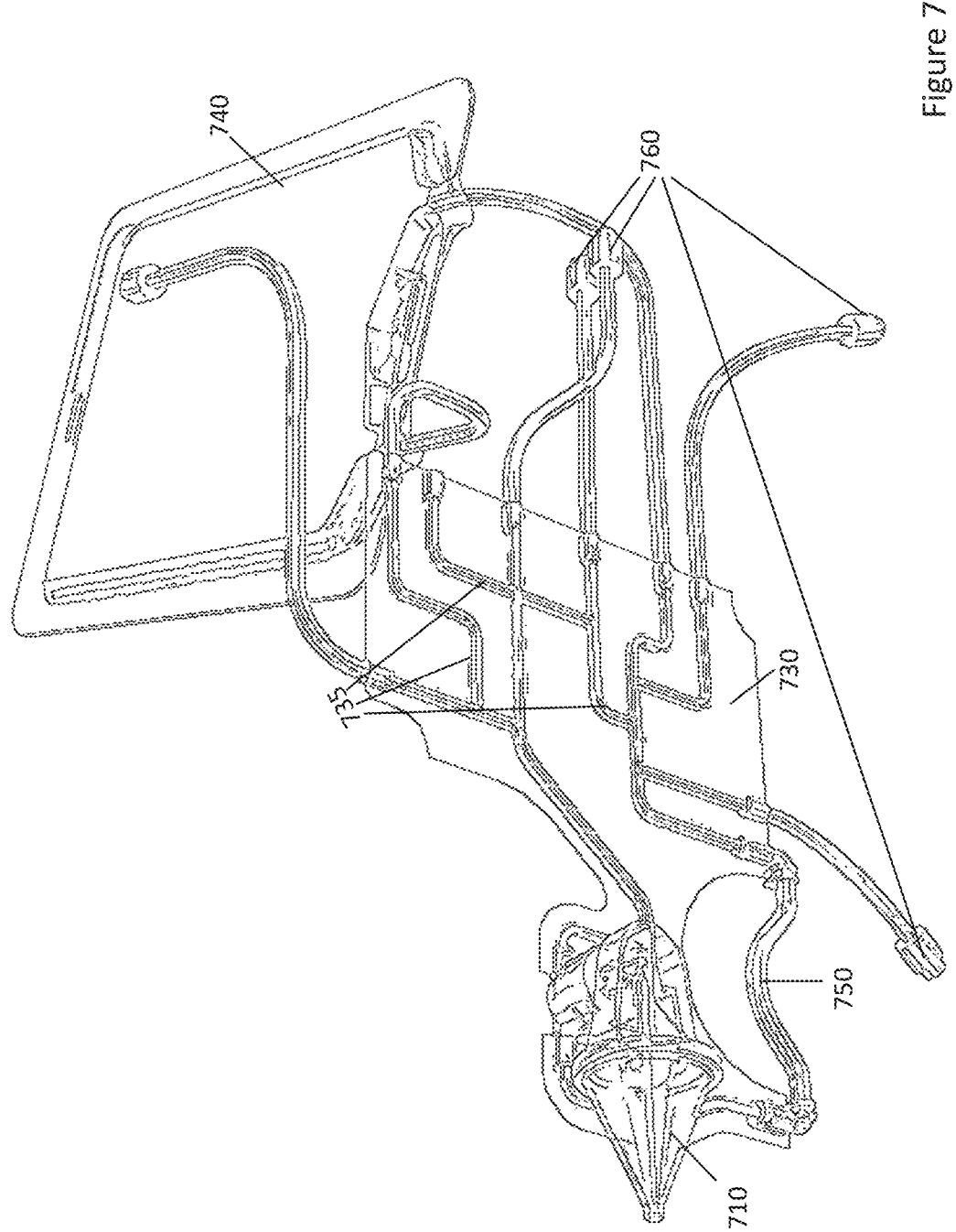
FIG. 7 shows an example of the fluid delivery manifold.
Figure 8A:
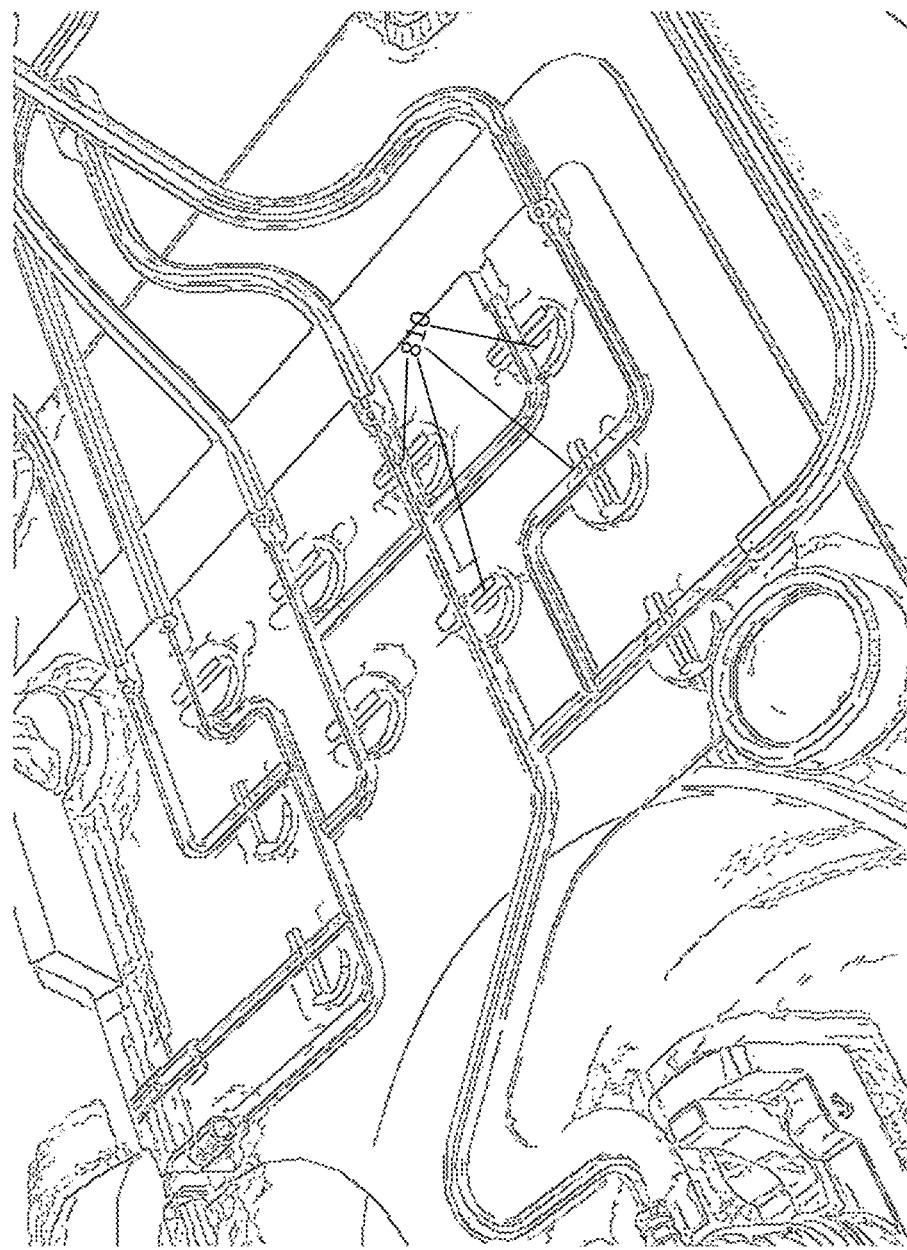

As illustrated in FIG. 6, the rotary coupling 160 also secures the separation chamber 610 to the fluid manifold 630. As shown in more detail in FIG. 7 the moulded manifold 730 presents a tubing network 735 to the instrument fluid control valves and sensors. FIG. 7 shows the manifold 730 with connected separation chamber 710 as may be supplied as a sterile disposable subsystem. The manifold 730 is connected to a number of external fluid lines connectors 760 for connection to other disposable kit and fluid supply components such as fluid bags for example. The manifold 730 tubing network 735 is configured to align with a valve actuation assembly as shown in FIG. 8. The valve actuation assembly comprises a plurality of pinch valve actuators 810 configured to, when actuated, close the respective fluid line by pinching the fluid line closed against the cover 740. As should be appreciated the preconfigured fluid lines of the manifold avoids the need for threading and fitting a complex of tubing and components into the instrument. This can significantly reduce operator errors. The instrument door locks the manifold into location and completes the pinch valve functionality when it is closed.

Figure 3E:
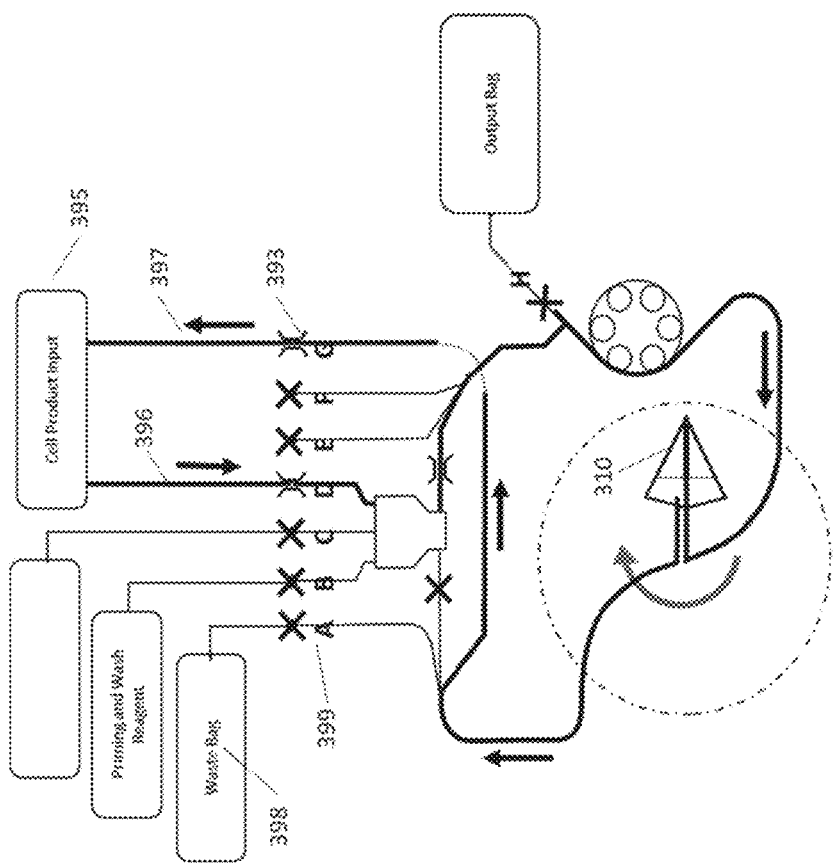

The manifold interfaces the fluidic network to the rotary coupling of the centrifuge. This creates a structure to resist the torsional reaction of the coupling with flexibility to compensate for geometric variations between the assemblies. It provides intimate coupling between the centrifugation environment and the static fluidics facilitating the very small volume recovery capability. The manifold can be designed for specific processing protocols to minimise the fluid volume within the system. Further, the manifold tubing network may be designed to allow different fluid paths to be selectively configured during processing by actuation of valves in combination. For example, FIGS. 3e and 3f illustrate how fluid flow may be selectively configured during processing, including a fluid path that may be configured to recirculate media fluid through the separation chamber. It should also be appreciated that opening and closing of valves is automated under control of the system processor.

The manifold can be manufactured using a method that can employ low cost tooling. This enables different process configurations to meet the unique detailed requirements embedded in many protocols to be developed at low cost. In an embodiment the manifold manufacture is achieved by a method described as twin sheet vacuum forming. This process is illustrated in FIG. 9. Two sheets of polymer approximately 0.6 mm in thickness are preheated and placed between heated plattens 910, 920. Vacuum is drawn to capture and form the sheets to each tool platten. The plattens 910, 920 are clamped closed and pressure is inserted between the two sheets by piercing the thin film 935 in header cavities 930 of the tool. The formed sheet can then be trimmed to provide the formed manifold 940. The combination of tool temperature, polymer pre-heating and pressure thermally bonds the polymer materials. A key objective is for the tool to be lowest cost possible. The tool design is focused on a single sided machining operation that can be completed in a single set-up on a computerized numerical control (CNC) machining centre. Tooling variants for short runs can be further reduced in cost by making the header cavities of the tool part of the fixed equipment infrastructure, and using process specific tooling inserts 925 for the plattens 910, 920. This combination of attributes is designed to enable end users of the centrifuge system to create process specific manifold configurations and have them provided within a practical cost.

The fixed manifold can have advantages for volume accuracy as there is less likelihood for error or variation introduced by human assembly of kit components. This is important for small volume processing as even millimeter variations in tube length may have significant impact on the overall internal system fluid volume. Process specific, fixed and preformed manifolds can also be design for minimizing internal system fluid volume. This can enable higher recovery concentrations, or in other words minimize dilution of the concentrated cells by media fluid by simply having less media fluid in the system. This is highly advantageous for small volume low cell (or other particle) count applications.

Figure 10:
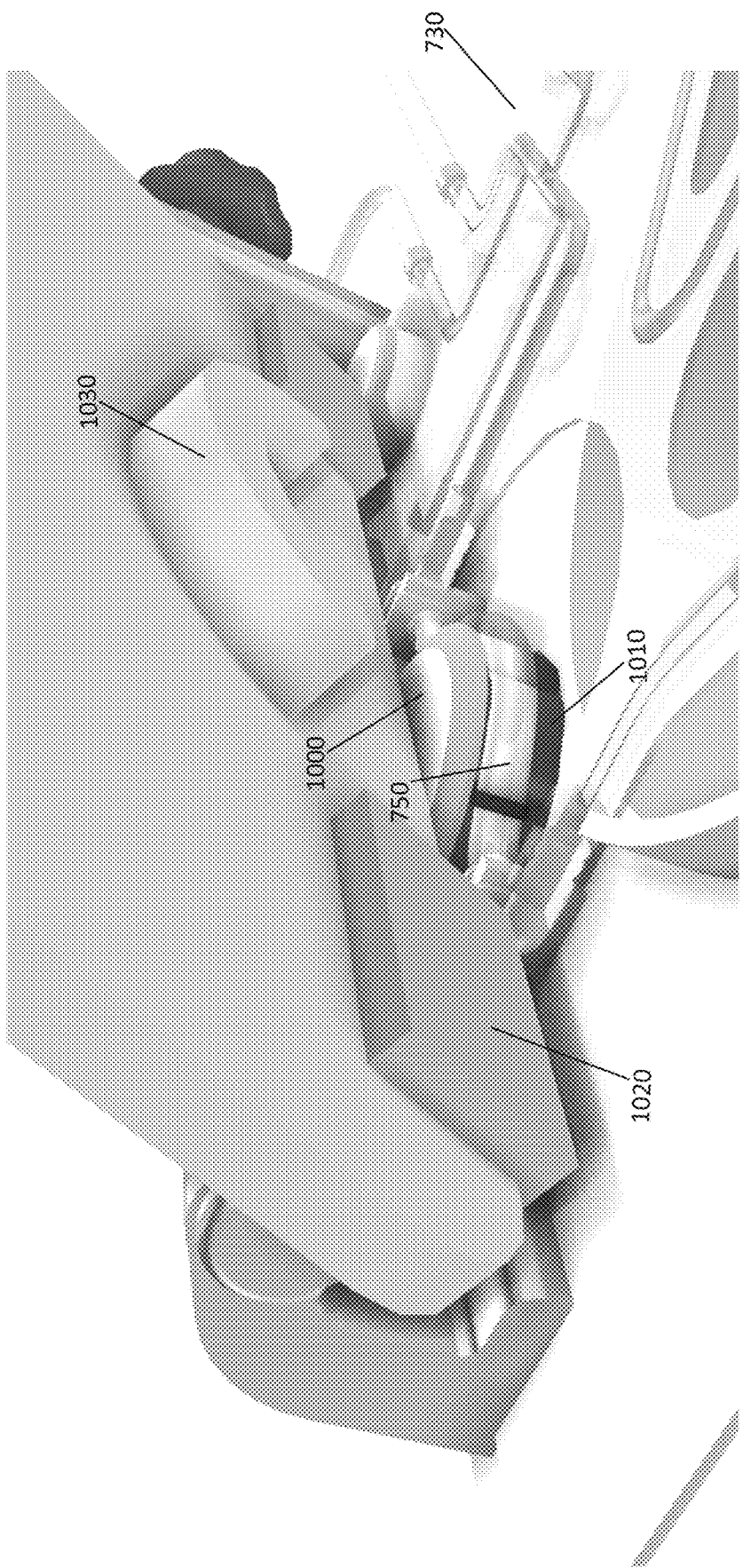
FIG. 10 illustrates an example of a pump interface.

The moulded manifold also supports the pump interface, as is illustrated in FIG. 10. Specialized tubing 750 for the peristaltic pump 1000 is attached to the manifold through moulded connectors. When the manifold 730 is loaded on the instrument the tubing naturally lies adjacent to the pump rollers 1010. A pump interface feature 1030 on the instrument door in combination with the door hinge geometry 1020 gathers the peristaltic pump tube and presses it against the pump roller assembly as the door closes. This eliminates errors in peristaltic pump loading. The pump interface feature 1030 attached to the door captures the peristaltic pump tubing and clamps it to the pump drive rollers with a controlled crush.

Figure 11:
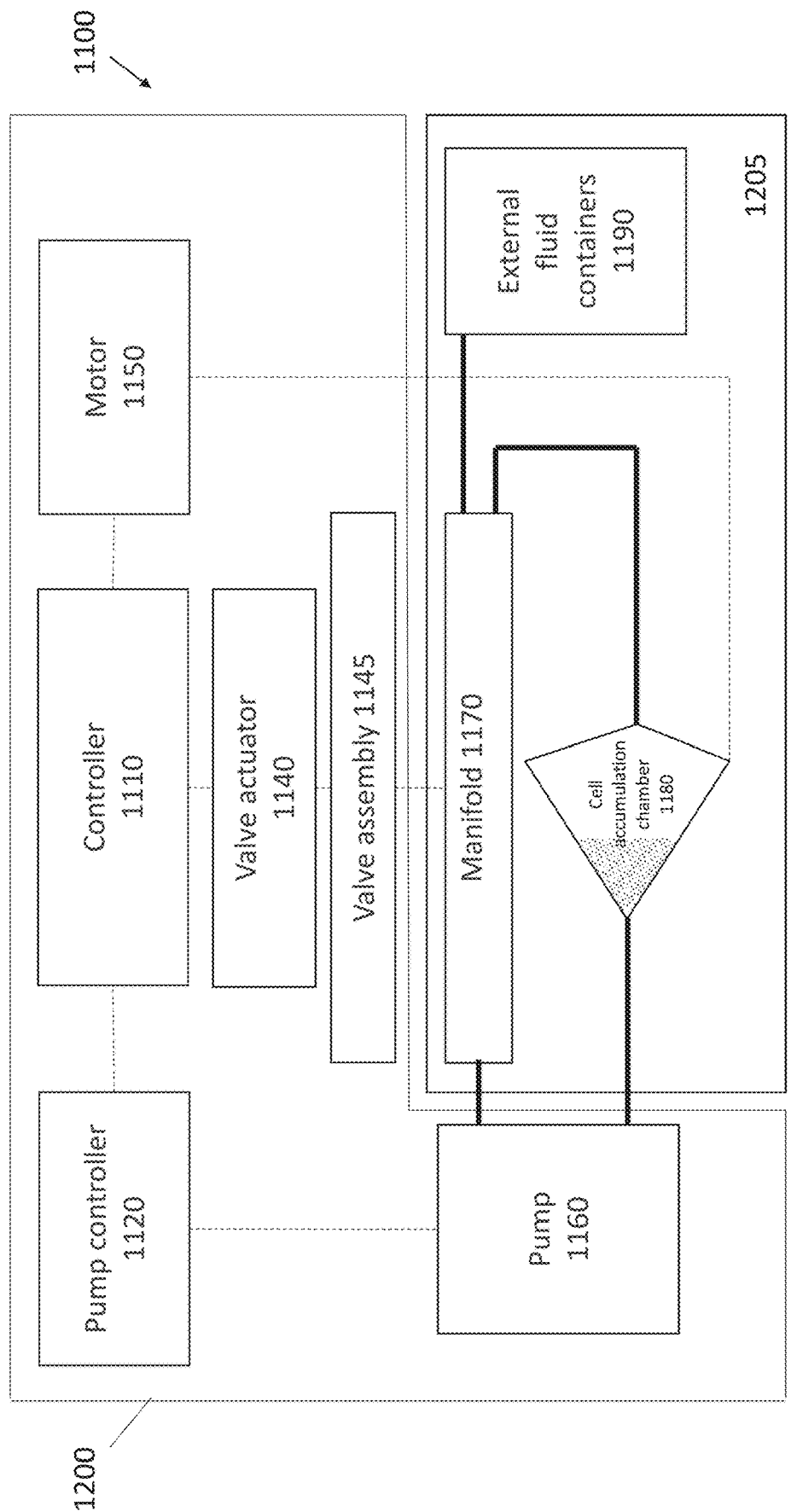
FIG. 11 is an exemplary block diagram of the components of an embodiment of the system.

As illustrated in FIG. 11, the system 1100 includes a controller 1110, such as a programmable microprocessor housed within the reusable subsystem 1200 to control operations of the motor 1150, pump 1120, 1160 and actuators 1140 of the valve assembly 1145. The controller may be programmed in accordance with a protocol to control an end to end separation process. The controller being configured to coordinate the motor and thereby chamber 1180 rotation speed and pumping rate as discussed above. The controller can also be configured to operate the valve actuators 1140 to cause opening and closing of individual valves in the valve assembly 1145 in accordance with the processing protocol. For example, to open valves for introduction of fluids from one or more external fluid containers 1190 connected to the manifold 1170, recirculation of fluids within the system by reconfiguring flow paths through the manifold, or for fluid recovery to an external chamber. It should be appreciated that in some embodiments the controller 1110 embedded within the system may be configured to control operation of the system components in a coordinated manner, and be linked (via a suitable wires or wireless data communication) to an external controller (for example an external computer system) controlling higher level processing protocol control. For example, an external computer system may be provided to enable enhanced user interface functionality and resources for functions such as monitoring, data capture and analytics. Using an external computer system may also enable greater flexibility in processing protocol design and programming for execution using the system. An external system may be used for controlling execution of the protocol, or for designing the protocol for downloading to the system for execution. Both of these embodiments are envisaged and considered particularly suitable for laboratory and trial environments. Also considered is an embodiment where the system is dedicated to a single processing protocol and the system controller may be fixed programmed (rather than downloadable) or use a dedicated processor such as an application specific integrated circuit. The fixed configuration of the system (i.e. manifold minimising risks of setup connection variation) and automated control can enable high consistency in processing outcomes. Further processing throughput may be improved making the same device feasible for both early stage experimentation, clinical trials and large scale operations.

It should be appreciated that embodiments of the present system may offer significant advantages over currently available centrifugation systems. The primary attributes of a cell washing technology are:

The largest volume of dilute cell suspension that can be collected.

The rate at which the dilute cell suspension can be processed while capturing the cells.

How small is the volume can the collected cells be delivered in.

The recovery of cells: % of cells delivered versus the cells supplied.

As a reverse flow centrifuge the recoveries are systematically in the 98% region, unsurpassed by any other cell handling methodology.

The rate of "harvesting" as the collection step is commonly described is governed by the fluid flow rate that the fluidized bed can tolerate without loss of cells from the fluidized bed. This is governed by the settling rate that can be achieved in the chamber that is reflected by the G's of acceleration. The design shown in FIG. 2 and FIG. 3 has been developed to operate up to 4000 G's but may be conservatively applied at 3000 G's, even this conservative use is three times the best offering for single-use reverse flow centrifugation in the market.

Embodiments of the disclosed system enable very small volume recovery. A stand out capability of this design is its ability to deliver the final product in a very low volume. A key objective of cell based therapeutic process development is to complete the entire process within a functionally closed single use environment. The final steps of many therapeutic product protocols require the entire cell product to be concentrated into a small volume. Commonly this is achieved through traditional "bucket" centrifugation steps conducted in high grade clean rooms with manual open intervention steps.

The embodiments described incorporate features specifically directed at high cell recovery in a low volume. Embodiments can include any combination of one of more of the features of:

Rotary coupling with direct axial interface to the supply tube

Small footprint to minimize flow distance from chamber, through pump to destination vessel.

Opportunity to embed an optical density sensor in the output line for selective capture and shut off.

These features combined with automated control of this step may enable a total fluid output volume less than 2 ml for cell populations of 10 million to 10 ml for 1 billion cells with high recovery.

Embodiments are configured to enable cost effective production. Many cell-based therapeutic products are based on transforming cells drawn from the patient into the therapeutic agent. These autologous therapies work with relatively small total cell populations. The capacity and functionality of this design makes it ideal to address the challenges presented by autologous products. Autologous products are commonly manufactured under cGMP (current Good Manufacturing Practise) that requires detailed process scrutiny and review and robust quality assurance testing before the product can be released for administration to the patient. To make such products affordable it is important to address every aspect of the cost. This design contributes by presenting an assembly of single use components that can be delivered at low cost.

Embodiments of the system are suitable for application in numerous processes for separating or accumulating small particles for recovery in a fluid suspension. Some examples of applications in the processing of cells for cell therapies include:

1) Cell concentration
2) Cell washing
3) Cell separation by a combination of concentration of larger, denser cells and elutriation of smaller, lighter cells and debris
4) Cell selection by separating cells attached to beads that may be either light or heavier than the surrounding cell population
5) formulation by adding a controlled volume of liquid (for example, cryoprotectant) to a known output volume of concentrated cells.

Although the system application examples discussed relate to cell processing, embodiments of the system may also be used for other applications. The reference to specific applications is bay way of example only and should not be considered as limiting the scope of the invention.

The system is designed to enable easy loading and minimise operator assembly errors. This instrument is designed for processing human cells for therapeutic purposes. It is important that the risk of process error is minimized in every way to avoid loss of precious material. This design incorporates a range of features to simplify loading of the disposable kit specifically to minimize risk of error. These features are embedded in the centrifuge chamber assembly and the manifold. The centrifuge chamber assembly and its interface with the centrifuge carrier present an intuitive interface supported by an audible click as the latch engages.

A significant advantage of the disclosed system, over currently available commercial systems, is that the configuration of the dip tube style separation chamber and rotary coupling enables this to be provided attached to the fluid delivery manifold as a preassembled clean single use kit. Further, the separation chamber requires minimal structural support from the motor mounting. This configuration also results in reduced kinetic energy during operation. Thus, this configuration significantly reduces the physical requirements on the reusable subsystem, enabling smaller size, less complexity and lower costs.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:
1. A compact reverse flow centrifuge system comprising:
a reusable subsystem; and
a single use, replaceable subsystem, the reusable subsystem comprising:
　a rotating motor head;
　a peristaltic pump;
　a valve assembly comprising one or more selectively operable pinch valve actuators;
　a system controller configured to control operation of the rotating motor head, the peristaltic pump, and the valve assembly in accordance with a programmed processing protocol; and
case housing the rotating motor head, the peristaltic pump, and the valve assembly, and the single use, replaceable subsystem comprising:
　a separation chamber comprising a substantially conical fluid enclosure portion connected to a neck portion, and having a dip tube extending centrally through the conical fluid enclosure from the neck portion to a conical tip of the conical fluid enclosure to provide a dip tube fluid path to the conical tip of the conical fluid enclosure, the neck portion further comprising an elution fluid path;
　a fluid delivery manifold comprising a first fluid port and a second fluid port configured for fluid communication with the separation chamber, a plurality of manifold fluid paths configured for connection to external fluid supply components for delivery of fluid to or from the first fluid port and the second fluid port, at least one of the plurality of manifold fluid paths being configured for engagement with at least one of the one or more pinch valve actuators of the valve assembly whereby the plurality of manifold fluid paths can be selectively opened or closed by operation of the one or more selectively operable pinch valve actuators of the valve assembly, and a pump engagement portion configured to enable operable engagement between the peristaltic pump and fluid paths to cause fluid flow within the plurality of manifold fluid paths of the fluid delivery manifold by operation of the peristaltic pump; and
　a rotary coupling connecting to the neck portion of the separation chamber through a rotational axis of the rotary coupling to connect the fluid delivery manifold to the separation chamber, and the rotary coupling having formed therein a first fluid communication path between the dip tube and the first fluid port, and a second fluid communication path between the elution fluid path and the second fluid port, the rotary coupling being configured to enable rotation of the separation chamber about the rotational axis through the neck portion relative to the fluid delivery manifold while the fluid delivery manifold is held in a fixed position by the case, and wherein the first fluid communication path communicating with the dip tube is aligned with the rotational axis,
　the neck portion of the separation chamber being further configured to engage with the rotating motor head which, in use, causes rotation of the separation chamber about the rotational axis, and
　the single use, replaceable subsystem being further configured to provide a closed environment for execution of reverse flow centrifugation processes.

2. A compact reverse flow centrifuge system as claimed in claim 1 wherein the fluid delivery manifold includes in each manifold fluid path at least one flexible portion configured to, in use, align with a respective one of the one or more selectively operable pinch valve actuators, whereby operation of each respective one of the selectively operable pinch valve actuator causes opening or closing of the manifold fluid path with which the respective one of the one or more selectively operable pinch valve actuators is aligned.

3. A compact reverse flow centrifuge system as claimed in claim 1 wherein when the plurality of manifold fluid paths of the fluid delivery manifold are attached using fluid connections to one or more external fluid vessels, including a cell suspension supply vessel, by actuation of the one or more selectively operable pinch valves actuators to selectively open or close the plurality of manifold fluid paths and operation of the peristaltic pump, a recirculating fluid flow is enabled to be selectively established though the fluid delivery manifold and the separation chamber, wherein the recirculating fluid flow delivers fluid from the cell suspension supply vessel though the fluid delivery manifold to the separation chamber via the first fluid communication path and the dip tube fluid path into the conical tip of the separation chamber during the rotation of the separation chamber to provide counter fluid flow within the separation chamber for establishment of a fluidized bed in the separation chamber, and via the second fluid communication path the fluid flow returns to the fluid delivery manifold for recirculation to the separation chamber through the fluid delivery manifold, whereby the fluidized bed in the chamber is established from the cell suspension supply vessel without risk of systematic cell losses.

4. A compact reverse flow centrifuge system as claimed in claim 1 wherein the fluid delivery manifold is configured to align the pump engagement portion with the peristaltic pump when the fluid delivery manifold is positioned in the case and wherein the case is configured to effect operative engagement of the pump engagement portion with the peristaltic pump when the case is closed and optionally the case is configured such that relative geometry of a case door and case door hinge gather a tube of the pump engagement portion into engagement with a peristaltic pump roller to effect the operative engagement with the peristaltic pump.

5. A compact reverse flow centrifuge system as claimed in claim 1 configured to operate at rotation speeds up to 8000 revolutions per minute.

6. A compact reverse flow centrifuge system as claimed in claim 5 wherein the conical fluid enclosure has a volume of 5 ml to 20 ml.

7. A compact reverse flow centrifuge system as claimed in claim 6 having a rotation radius of 50 to 70 mm.

8. A compact reverse flow centrifuge system as claimed in claim 1 configured for cell therapies to enable fluid volume recoveries from 1 ml to 10 ml for 10 million to 2 billion cells.

9. A compact reverse flow centrifuge system as claimed in claim 1 configured to operate at rotation speeds up to 200,000 revolutions per minute.

10. A compact reverse flow centrifuge system as claimed in claim 9 wherein the conical fluid enclosure has a volume of 0.1 ml to 0.5 ml.

11. A compact reverse flow centrifuge system as claimed in claim 10 having a tip rotation radius of 10 to 30 mm.

12. A separation chamber for a compact reverse flow centrifuge system, the separation chamber comprising:

a substantially conical fluid enclosure portion having a conical tip;

a neck portion connected to the substantially conical fluid enclosure portion;

a dip tube extending centrally through the conical fluid enclosure from the neck portion to the conical tip to provide a dip tube fluid path to the conical tip of the conical fluid enclosure;

an elution path through the neck portion;

a rotary coupling connected to the neck portion through a rotational axis of the rotary coupling, the rotary coupling having formed therein a first fluid communication path to the dip tube for fluid communication with a first fluid port for connection to a fluid delivery manifold, and a second fluid communication path to an elution fluid path through the neck portion for fluid communication with a second fluid port for connection to the fluid delivery manifold, wherein the first fluid communication path communicating with the dip tube is aligned with the rotational axis, the rotary coupling enabling rotation of the separation chamber about the rotational axis through the neck portion relative to the first fluid port and the second fluid port; and the neck portion being further configured to engage with a rotating motor head which, in use, causes rotation of the separation chamber about the rotational axis.

13. A separation chamber as claimed in claim 12 wherein the first fluid communication path is provided by a tube through an axle of the rotary coupling and the second fluid communication path is through a coaxial cannula.

14. A separation chamber as claimed in claim 12 wherein the elution fluid path through the neck portion comprises a plurality of fluid paths from the conical fluid enclosure to the elution path in the neck portion in fluid communication with the second fluid communication path through the rotary coupling.

15. A separation chamber as claimed in claim 14 wherein the separation chamber includes a wall separating the conical fluid enclosure from the neck portion, the wall having apertures formed therein to provide the plurality of fluid paths to the elution path in the neck portion.

16. A separation chamber as claimed in claim 12 wherein the conical tip includes a fluid channeling structure configured to cause dispersal of fluid introduced via the dip tube through the conical fluid enclosure.

17. A separation chamber as claimed in claim 12 wherein the conical fluid enclosure has a volume of 5 ml to 20 ml.

18. A separation chamber as claimed in claim 12 having a tip rotation radius of 50 to 70 mm.

19. A separation chamber as claimed in claim 18 having a cone diameter of 35 mm and cone height of 38 mm.

20. A separation chamber as claimed in claim 12 wherein the conical fluid enclosure has a volume of 0.1 ml to 0.5 ml.

21. A separation chamber as claimed in claim 12 having a tip rotation radius of 10 to 30 mm.

* * * * *